(12) United States Patent
Chandraratna et al.

(10) Patent No.: US 10,517,843 B2
(45) Date of Patent: Dec. 31, 2019

(54) RECEPTOR SUBTYPE AND FUNCTION SELECTIVE RETINOID AND REXINOID COMPOUNDS IN COMBINATION WITH IMMUNE MODULATORS FOR CANCER IMMUNOTHERAPY

(71) Applicant: Io Therapeutics, Inc., Houston, TX (US)

(72) Inventors: Roshantha A. Chandraratna, San Juan Capistrano, CA (US); Martin E. Sanders, Seattle, WA (US)

(73) Assignee: Io Therapeutics, Inc., Houston, TX (US)

( * ) Notice: Subject to any disclaimer, the term of this patent is extended or adjusted under 35 U.S.C. 154(b) by 0 days.

(21) Appl. No.: 16/428,142

(22) Filed: May 31, 2019

(65) Prior Publication Data

US 2019/0282524 A1   Sep. 19, 2019

Related U.S. Application Data

(62) Division of application No. 16/281,402, filed on Feb. 21, 2019, which is a division of application No. 16/034,064, filed on Jul. 12, 2018, now Pat. No. 10,231,944.

(60) Provisional application No. 62/532,233, filed on Jul. 13, 2017, provisional application No. 62/552,814, filed on Aug. 31, 2017.

(51) Int. Cl.
| | |
|---|---|
| *A61K 39/00* | (2006.01) |
| *A61K 31/196* | (2006.01) |
| *C07K 16/28* | (2006.01) |
| *A61K 31/5513* | (2006.01) |
| *A61K 39/395* | (2006.01) |
| *A61P 35/00* | (2006.01) |
| *A61P 35/02* | (2006.01) |
| *C07K 16/30* | (2006.01) |
| *A61K 31/505* | (2006.01) |
| *A61K 31/47* | (2006.01) |
| *A61K 31/4436* | (2006.01) |
| *A61K 31/382* | (2006.01) |
| *A61K 31/195* | (2006.01) |
| *A61K 31/192* | (2006.01) |
| *C12N 5/0783* | (2010.01) |
| *A61K 45/06* | (2006.01) |
| *A61K 31/353* | (2006.01) |

(52) U.S. Cl.
CPC .......... *A61K 31/196* (2013.01); *A61K 31/192* (2013.01); *A61K 31/195* (2013.01); *A61K 31/353* (2013.01); *A61K 31/382* (2013.01); *A61K 31/4436* (2013.01); *A61K 31/47* (2013.01); *A61K 31/505* (2013.01); *A61K 31/5513* (2013.01); *A61K 39/0011* (2013.01); *A61K 39/3955* (2013.01); *A61K 45/06* (2013.01); *A61P 35/00* (2018.01); *A61P 35/02* (2018.01); *C07K 16/2803* (2013.01); *C07K 16/2818* (2013.01); *C07K 16/2878* (2013.01); *C07K 16/30* (2013.01); *C12N 5/0638* (2013.01); *A61K 2039/505* (2013.01); *A61K 2039/5156* (2013.01); *A61K 2039/5158* (2013.01); *C07K 2317/622* (2013.01); *C07K 2319/03* (2013.01); *C07K 2319/33* (2013.01); *C12N 2501/999* (2013.01)

(58) Field of Classification Search
CPC .................................................. A61K 31/196
See application file for complete search history.

(56) References Cited

U.S. PATENT DOCUMENTS

| | | |
|---|---|---|
| 4,326,055 A | 4/1982 | Loeliger |
| 4,362,892 A | 12/1982 | Hindley |
| 5,234,926 A | 8/1993 | Chandraratna |
| 5,324,840 A | 6/1994 | Chandraratna |
| 5,612,356 A | 3/1997 | Yoshimura et al. |
| 5,723,666 A | 3/1998 | Vuligonda et al. |
| 5,739,338 A | 4/1998 | Beard et al. |
| 5,776,699 A | 7/1998 | Klein et al. |
| 5,824,685 A | 10/1998 | Campochiaro et al. |
| 5,877,207 A | 3/1999 | Klein et al. |
| 5,919,970 A | 7/1999 | Song et al. |
| 5,958,954 A | 9/1999 | Klein et al. |
| 6,037,488 A | 3/2000 | Song et al. |
| 6,225,494 B1 | 5/2001 | Song et al. |
| 6,387,950 B2 | 5/2002 | Nehme et al. |
| 6,452,032 B1 | 9/2002 | Beard et al. |
| 6,455,701 B1 | 9/2002 | Song et al. |
| 6,653,322 B1 | 11/2003 | Chambon et al. |
| 6,942,980 B1 | 9/2005 | Klein |
| 7,476,673 B2 | 1/2009 | Tsang |
| 9,907,768 B2 | 3/2018 | Chandraratna et al. |

(Continued)

FOREIGN PATENT DOCUMENTS

| | | |
|---|---|---|
| CA | 2974066 | 6/2016 |
| EP | 0661259 | 7/1995 |

(Continued)

OTHER PUBLICATIONS

Johnson et al., "Synthesis and characterization of a highly potent and effective antagonist of retinoic acid receptors." J Med Chem, 38:4764-4767 (1995).
Naidoo et al., "Immune modulation for cancer therapy." Br. J. Cancer, 111:2214-2219 (2014).
Hodi et al., "Improved survival with ipilimumab in patients with metastatic melanoma." NEJM, 363:711-723 (2010).
Keir et al., "PD-1 and its ligands in tolerance and immunity." Ann Rev Immunol, 26:677-704 (2008).
Topolian et al., "Safety, activity, and immune correlates of anti-PD-1 antibody in cancer." NEJM, 366:2443-3454 (2012).

(Continued)

*Primary Examiner* — Sheela J. Huff
(74) *Attorney, Agent, or Firm* — K&L Gates LLP; Louis C. Cullman; David Diamond

(57) ABSTRACT

Disclosed herein are methods for culturing CAR-modified immune cells with at least one Retinoic Acid Receptor and/or Retinoid X Receptor active agent.

17 Claims, 2 Drawing Sheets

(56) References Cited

U.S. PATENT DOCUMENTS

| | | | |
|---|---|---|---|
| 10,004,708 | B2 | 6/2018 | Chandraratna |
| 10,004,709 | B2 | 6/2018 | Chandraratna |
| 10,123,982 | B2 | 11/2018 | Chandraratna |
| 10,213,401 | B2 | 2/2019 | Chandraratna |
| 10,231,944 | B2 | 3/2019 | Chandraratna |
| 2001/0018456 | A1 | 8/2001 | Fesus et al. |
| 2005/0148590 | A1 | 7/2005 | Tsang |
| 2005/0259203 | A1 | 11/2005 | Kimura |
| 2007/0077652 | A1 | 4/2007 | Peled |
| 2008/0300312 | A1 | 12/2008 | Chandraratna |
| 2009/0176862 | A1 | 7/2009 | Chandraratna et al. |
| 2009/0181988 | A1 | 7/2009 | Welsh |
| 2009/0203720 | A1 | 8/2009 | Zhao |
| 2011/0150892 | A1 | 6/2011 | Thudium et al. |
| 2014/0086909 | A1 | 3/2014 | Lu |
| 2014/0286973 | A1 | 9/2014 | Powell, Jr. |
| 2015/0290194 | A1 | 10/2015 | Wang et al. |
| 2016/0067336 | A1 | 3/2016 | Fandi et al. |
| 2016/0075783 | A1 | 3/2016 | King et al. |
| 2016/0317654 | A1 | 11/2016 | Noelle |
| 2017/0136063 | A1 | 5/2017 | Perez et al. |
| 2017/0354623 | A1 | 12/2017 | Chandraratna |
| 2018/0133179 | A1 | 5/2018 | Chandraratna et al. |
| 2018/0133180 | A1 | 5/2018 | Chandraratna et al. |
| 2018/0133181 | A1 | 5/2018 | Chandraratna et al. |
| 2018/0133182 | A1 | 5/2018 | Chandraratna et al. |
| 2018/0133183 | A1 | 5/2018 | Chandraratna et al. |
| 2018/0338940 | A1 | 11/2018 | Chandraratna |
| 2018/0338941 | A1 | 11/2018 | Chandraratna |
| 2019/0015363 | A1 | 1/2019 | Chandraratna |
| 2019/0105292 | A1 | 4/2019 | Chandraratna |
| 2019/0167617 | A1 | 6/2019 | Chandraratna et al. |

FOREIGN PATENT DOCUMENTS

| | | | |
|---|---|---|---|
| WO | 2001/007028 | A2 | 2/2001 |
| WO | 2002/028810 | A2 | 4/2002 |
| WO | 2007/041398 | A2 | 4/2007 |
| WO | 2008/121570 | | 10/2008 |
| WO | 2015/092420 | A1 | 6/2015 |
| WO | 2016/144976 | A1 | 9/2016 |
| WO | 2017/031367 | | 2/2017 |
| WO | 2017/091762 | | 6/2017 |
| WO | 2017/214575 | A1 | 12/2017 |
| WO | 2019/014468 | | 1/2019 |
| WO | 2019/014492 | | 1/2019 |
| WO | 2019/046591 | | 3/2019 |

OTHER PUBLICATIONS

Holmgaard et al., Indoleamine 2,3-dioxygenase is a critical resistance mechanism in antitumor T cell Immunotherapy targeting CTLA-4. J Exp Med, 210:1389-1402 (2013).
Munn et al., "Indoleamine 2,3-dioxygenase and tumor-induced tolerance." J Clin Invest, 117:1147-1154 (2007).
Mucida et al., "Reciprocal TH17 and regulatory T cell differentiation mediated by retinoic acid." Science, 317:256-260 (2007).
Pino-Lagos et al., "A retinoic acid-dependent checkpoint in the development of CD4+ T cell-mediated immunity." J Exp Med, 208:1767-1775 (2011).
Nowak et al., "Treatment with retinoid X receptor agonist IRX4204 ameliorates experimental autoimmune encephalomyelitis." Am J Translational Res, 8:1016-1026 (2016).
Curiel et al., "Specific recruitment of regulatory T cells in ovarian carcinoma fosters immune privilege and predicts reduced survival." Nat Med, 10:942-949 (2004).
Teng et al., "Identification of highly potent retinoic acid receptor alpha-selective antagonists." J Med Chem, 40:2445-2451 (1997).
International Search Report and Written Opinion for International Application No. PCT/US2017/036870 dated Sep. 6, 2017.
Jones et al., "A phase I study of tazarotene in adults with advanced cancer." British Journal of Cancer, 89:808-815 (2003).
Gargett et al., "GD2-specific CAR T cells undergo potent activation and deletion following antigen encounter but can be protected from activation-induced cell death by PD-1 blockade." Molecular Therapy, vol. 24, No. 6, pp. 1135-1149 (2016).
Ghiaur et al., "Regulation of human hematopoietic stem cell self-renewal by the microenvironment's control of retinoic acid signaling." Proc Natl Acad Sci USA, 110(40):16121-16126 (2013).
Huff et al., "The paradox of response and survival in cancer therapeutics." Blood, vol. 107, No. 2, pp. 431-434 (2006).
Johnson et al., "Synthesis and biological activity of high-affinity retinoic acid receptor antagonists." Bioorganic & Medicinal Chemistry, 7:1321-1338 (1999).
Kane et al., "HPLC/UV quantitation of retinal, retinol, and retinyl esters in serum and tissues." Anal Biochem, 378(1):71-79 (2008).
Koneru et al., "A phase I clinical trial of adoptive T cell therapy using IL-12 secreting MUC-16ecto directed chimeric antigen receptors for recurrent ovarian cancer." Journal of Translational Medicine, 13:102 (2015).
Locke et al., "Phase 1 results of ZUMA-1: A multicenter study of KTE-C19 anti-CD19 CAR T cell therapy in refractory aggressive lymphoma." Molecular Therapy, vol. 25, No. 1, pp. 285-295 (2017).
Long et al., "Reduction of MDSCs with all-trans retinoic acid improves CAR therapy efficacy for sarcomas." Cancer Immunol Res, 4(10):869-880 (2016).
Makita et al., "Clinical development of anti-CD19 chimeric antigen receptor T-cell therapy for B-cell non-Hodgkin lymphoma." Cancer Sci, 108:1109-1118 (2017).
M,S., "Bone marrow (BM) stromal expression of cytochrome P450 (CYP) enzymes protects acute myeloid leukemia (AML) from all-trans retinoic acid (ATRA)." Blood, 122: p. 1449a (2013).
Su et al., "All-trans retinoic acid acitivity in acute myeloid leukemia: Role of cytochrome P450 enzyme expression by be microenvironment." PLOS One, 14pp (2015).
Tobita et al., "Treatment with a new synthetic retinoid, Am80, of acute promyelocytic leukemia relapsed from a complete remission induced by all-trans retinoic acid." Blood, 90(3): 967-973 (1997).
Verfaille et al., "Oral R115866 in the treatment of moderate to severe plaque-type psoriasis." J Eur Acad Dermatol Venereol, 21(8):1038-1046 (2007).
Yoshida et al., "All-trans retinoic acid enhances cytotoxic effect of T cells with an anti-CD38 chimeric antigen receptor in acute myeloid leukemia." Clinical & Translational Immunology, 5, e116 (2016).
Jetson et al., "Practical synthesis of a chromene analog for use as a retinoic acid receptor alpha antagonist lead compound." European Journal of Medicinal Chemistry, vol. 63, pp. 104-108 (2013).
U.S. Appl. No. 16/281,402, filed Feb. 21, 2019.
Mihara et al., "All-trans retinoic acid and interferon-alpha increase CD38 expression on adult T cell leukemia cells and sensitize them to T cells bearing anti-CD38 chimeric antigen receptors." Blood Cancer Journal, 6, e. 421 (2016).
Invitation to pay additional fees in PCT/US2018/048876; dated Oct. 9, 2018.
Porter et al., "Chimeric Antigen Receptor-Modified T Cells in Chronic Lymphoid Leukemia." New England Journal of Medicine, 365(8): 1-12 (2011).
Davila et al., "CD-19-Targeted CAR T Cells as Novel Cancer Immunotherapy for Relapsed or Refractory B Cell Acute Lymphoblastic Leukemia." Clinical Advances in Hematology & Oncology, 14(10):1-11 (2016).
Davila et al., CAR Therapy for CLL: What are the Challenges? Hematology/Oncology Clinics of North America, 27(3):1-16 (2013).
Brudno et al., Toxicities of chimeric antigen receptor T cells: recognition and management. Blood, 127(26):3321-3330 (2016).
Toma et al., RARalpha Antagonist RO 41/5253 Inhibits Proliferation and Induces Apoptosis in Breast Cancer Cells Lines. International Journal of Cancer, 78:86-94 (1998).
Szondy et al., Induction of Apoptosis by Retinoids and Retinoic Acid Receptor Gamma-Selective compound in Mouse Thymocytes through a Novel Apoptosis Pathway. Molecular Pharmacology 51:972-982 (1997).
Johnson et al., Retinoid X Receptor (RXR) Agonist-Induced Activation of the Dominant-Negative RAR-Retinoic Acid Receptor

(56) References Cited

OTHER PUBLICATIONS alpha4β3 Heterodimers is Developmentally Regulated during Myeloid Differentiation. Molecular and Cellular Biology, 19(5):3372-3382 (1999).
National Center for Biotechnology Information. PubChem Compound Database; CID=24785198.
International Search Report and Written Opinion for PCT/US2018/041862; dated Oct. 15, 2018.
Alonso et al., "Hedgehog and retinoid signaling alters multiple myeloma microenvironment and generates ortezomib resistance." J. Cid,. Invent., 126(12):4460-4468 (2016).
Sharpe & Mount, "Genetically modified T cells in cancer therapy:opportunities and challenges." Dis. Model Mech., 8(4):337-350 (2015).
International Search Report and Written Opinion for PCT/US2018/041892; dated Sep. 20, 2018.

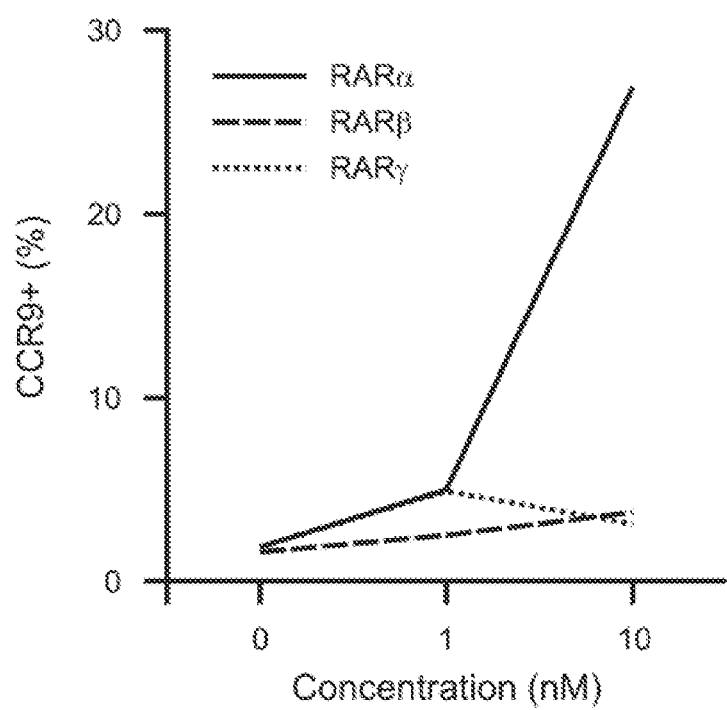

RECEPTOR SUBTYPE AND FUNCTION SELECTIVE RETINOID AND REXINOID COMPOUNDS IN COMBINATION WITH IMMUNE MODULATORS FOR CANCER IMMUNOTHERAPY

RELATED APPLICATIONS

This application is a divisional of U.S. patent application Ser. No. 16/281,402, filed Feb. 21, 2019, which is a divisional of U.S. patent application Ser. No. 16/034,064, filed Jul. 12, 2018, now U.S. Pat. No. 10,231,944, which claims the benefit of U.S. Provisional Patent Applications No. 62/532,233, filed on Jul. 13, 2017 and 62/552,814, filed on Aug. 31, 2017. The entire contents of which are each incorporated by reference herein.

BACKGROUND

For years, the cornerstones of cancer treatment have been surgery, chemotherapy, and radiation therapy. Over the last decade, targeted therapies—drugs that target cancer cells by homing in on specific molecular changes seen primarily in those cells—have also emerged as standard treatments for a number of cancers. One approach to immunotherapy involves engineering immune cells to recognize and attack tumors.

SUMMARY

Disclosed herein are compounds for potentiation of targeted cancer immunotherapeutics. Compounds which act on retinoic acid receptors (RAR) and retinoid X receptors (RXR) are used in combination with chimeric antigen receptor (CAR)-modified immune cells (sometimes abbreviated as CAR-MIC) to potentiate the anti-cancer activity.

Thus, provided herein are methods of treating cancer, the methods comprising administering CAR-modified immune cells and at least one retinoid active agent and/or rexinoid active agent (collectively RAR/RXR active agents). In some embodiments, the retinoid active agent is a Retinoic Acid Receptor (RAR) active agent. In some embodiments, the rexinoid active agent is a Retinoid X Receptor (RXR) active agent. In some embodiments, two RAR/RXR active agents are used; they can be two RAR active agents, two RXR active agents, or a RAR active agent and a RXR active agent. In some embodiments the RAR/RXR active agent acts as an agonist of its receptor while in other embodiments the RAR/RXR active agent acts as an antagonist of its receptor. In some embodiments utilizing multiple RAR/RXR active agents, the multiple RAR/RXR active agents are formulated and administered separately. In some aspects of these embodiments, the RAR/RXR active agents are administered separately, but during the same treatment session. In other aspects of these embodiments, the RAR/RXR active agents are administered in different treatment sessions. In other embodiments, the multiple RAR/RXR active agents are formulated separately, but co-administered (that is, administered during the same treatment session). In still other embodiments, the multiple RAR/RXR active agents are formulated together as a single, common medicament.

In some embodiments, the CAR-modified immune cells are, or comprise, CAR-modified T cells. In some embodiments, the CAR-modified immune cells are, or comprise, CAR-modified NK cells. In some embodiments, the CAR-modified immune cells are, or comprise, CAR-modified NKT cells. In some embodiments, the CAR-modified immune cells are, or comprise, CAR-modified macrophages. Further embodiments can comprise mixtures of these cell types. Most typically such cellular preparations are administered by infusion, for example intravenous infusion. In contrast, the RAR/RXR active agents are small molecules that can be administered orally, for example as pills or capsules and the like. Thus the RAR/RXR active agents and the CAR-modified immune cells may be administered on independent schedules.

In some embodiments, the retinoid active agent is a RARα antagonist. In some embodiments, the RARα antagonist is a compound of general formula (I):

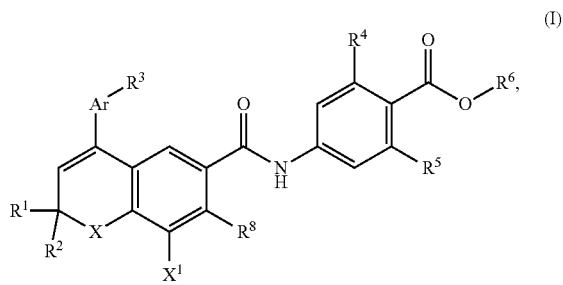

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH.

In some embodiments, the RARα antagonist is AGN194301, AGN193491, AGN193618, AGN194202, or AGN194574.

In some embodiments, the RARα antagonist is a compound of general formula (II):

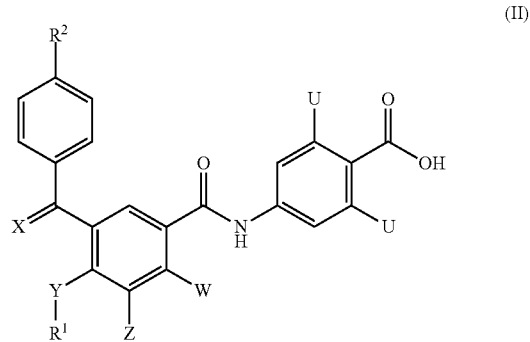

wherein $R^1$ and $R^2$ are independently $C_{1-6}$ alkyl; X is O, S, or $CH_2$; Y is P, S, $CH_2$, or $NR^3$, wherein $R^3$ is $C_{1-6}$ alkyl; Z is Cl or Br; W is H or OH; and U is independently H or F.

In some embodiments, the RARα antagonist is:

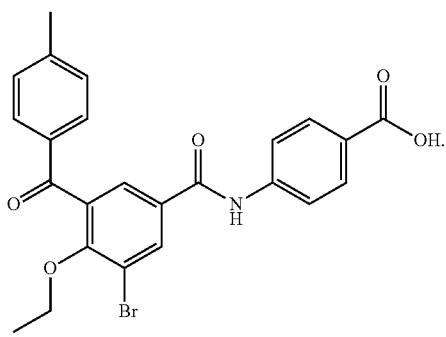

VTP 196696

In some embodiments, the RARα antagonist is a compound of general formula (III):

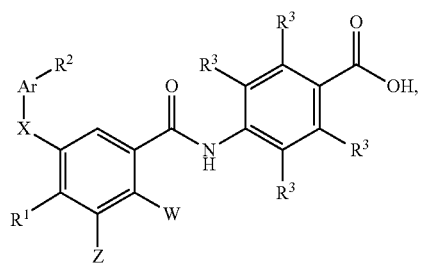

(III)

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br.

In some embodiments, the RARα antagonist is:

AGN 194777

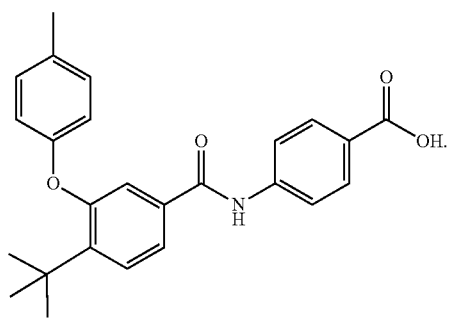

In some embodiments, the RARα antagonist is

BMS185411

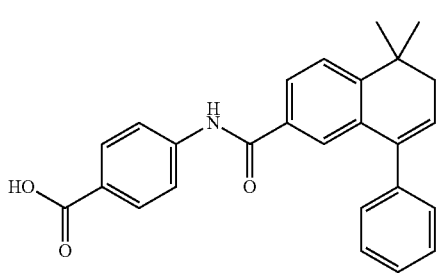

BMS614

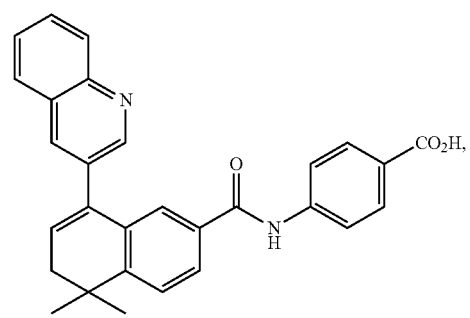

Ro41-5253

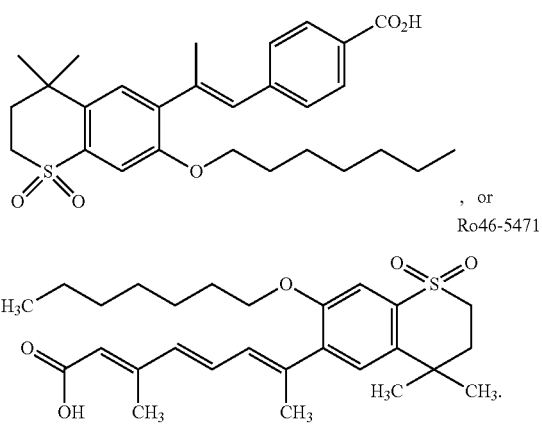

, or

Ro46-5471

In some embodiments, the retinoid active agent is a RAR agonist. In some embodiments, the RAR agonist is:

AGN 190183

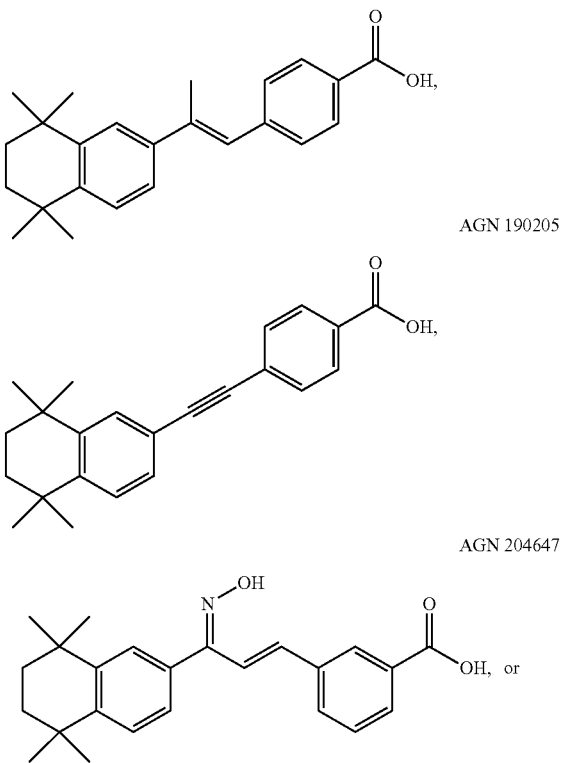

AGN 190205

AGN 204647

, or

AGN 190168 (Tazarotene)

In some embodiments, the RAR agonist is a RARγ selective agonist of general formula (IV):

(IV)

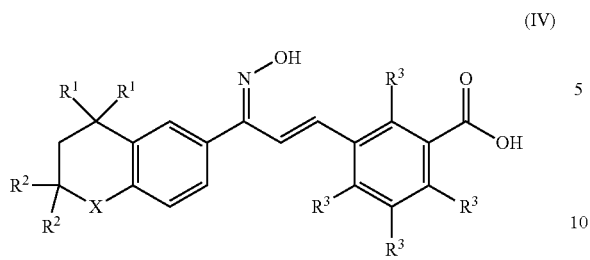

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl.

In some embodiments, the RAR agonist is a RARγ selective agonist selected from

CD437

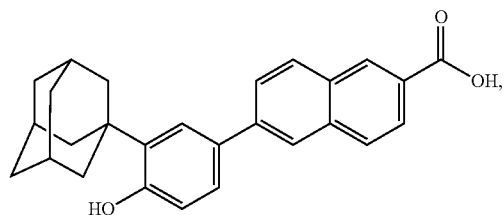

CD2325

CD666

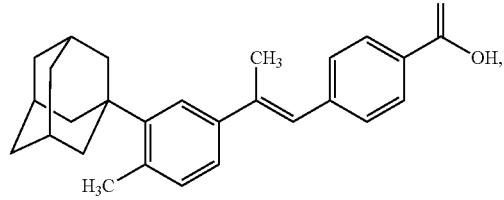

BMS961

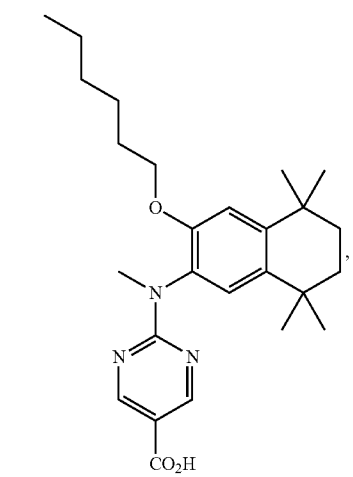

and

In some embodiments, the retinoid active agent is a RXR antagonist. In some embodiments, the RXR antagonist is:

HX 531

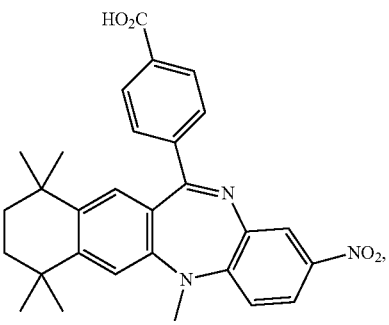

PA 451

PA 452

LG 100754

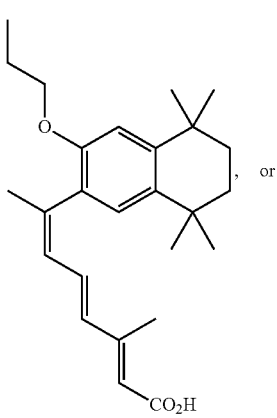

-continued

UVI 3003

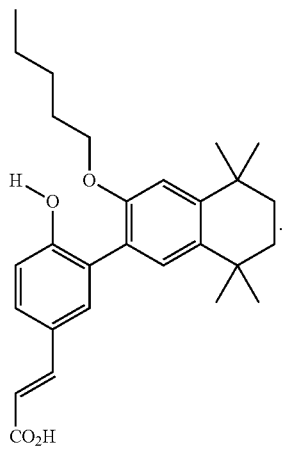

In some embodiments, the RXR antagonist is AGN195393, or LGN100849.

In some embodiments, the methods comprise additionally administering at least one cancer chemotherapy agent.

In some embodiments, the methods comprise administering at least two retinoid active agents. In some embodiments, the two retinoid active agents are a RARα antagonist and a RARγ agonist.

In some embodiments, the methods further comprise administering to the subject at least one immune checkpoint inhibitor. In some embodiments, the immune checkpoint inhibitor is an inhibitor of at least one of CTLA-4, PD-1, TIM-3, LAG-3, PD-L1 ligand, B7-H3, B7-H4, BTLA, or is an ICOS, or OX40 agonist. In some embodiments, the immune checkpoint inhibitor is an antibody specific for at least one of CTLA-4, PD-1, TIM-3, LAG-3, PD-L1 ligand, B7-H3, B7-H4, BTLA, ICOS, or OX40.

Also disclosed herein are methods of prolonging the disease-free survival of a cancer patient comprising administering CAR-modified immune cells and at least one retinoid active agent and/or rexinoid active agent.

Also disclosed herein are methods of decreasing toxicity of CAR-modified immune cells comprising administering to a subject in need thereof at least one retinoid active agent and/or rexinoid active agent in combination with the CAR-modified immune cells such that as a result of the combination, a lower dose of CAR-modified immune cells are administered more safely and equally effectively than if the CAR-modified immune cells were administered alone; or that a higher dose of CAR-MIC can be administered with greater efficacy and equal safety.

Also disclosed herein are methods of expanding the number of CAR-modified immune cells comprising culturing the CAR-modified immune cells in a culture medium comprising at least one retinoid active agent and/or rexinoid active agent. In some embodiments this is done instead of administering RAR/RXR active agent(s) to the patient. In other embodiments this is done in addition to administering RAR/RXR active agent(s) to the patient. In various embodiments the RAR/RXR active agent(s) used in the CAR-modified immune cell culture and those administered to the patient are different, the same, or one set constitutes a subset of the other.

Also disclosed herein are methods of treating cancer comprising administering to a subject in need thereof, chimeric antigen receptor (CAR)-modified immune cells, at least one retinoid active agent and/or rexinoid active agent, and at least one immune checkpoint inhibitor.

BRIEF DESCRIPTION OF THE DRAWINGS

FIG. 1A-C shows that RAR receptor specific agonists regulate FoxP3, α4β7, and CCR9 expression. Purified CD4$^+$ CD25$^-$ FoxP3$^-$ cells were cultured in media with the specified concentration of each RAR agonist and analyzed by flow cytometry for FoxP3 (FIG. 1A), α4β7 (FIG. 1B), and CCR9 (FIG. 1C) expression in total CD4 T cells. FoxP3 results are representative of 3 independent experiments. CCR9 and α4β7 results are representative of multiple experiments.

DETAILED DESCRIPTION

Figure 1A:
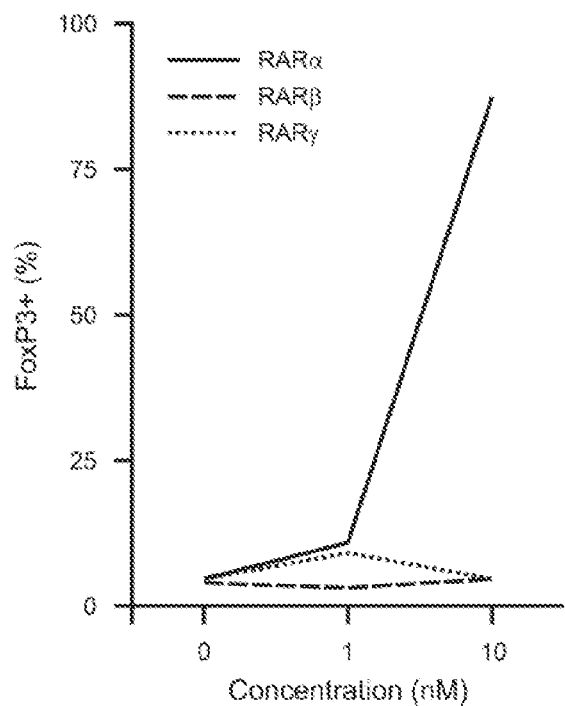

Disclosed herein are combinations for therapy of cancer comprising retinoid and/or rexinoid compounds and adoptive transfer of immune cells expressing chimeric antigen receptors (CAR-modified immune cells or CAR-MIC). Compounds which act on retinoic acid receptors (RAR) and/or retinoid X receptors (RXR) augment the activity of CAR-modified immune cells. By potentiation it is meant that the CAR-modified immune cells have greater and/or more rapid effect when the RAR/RXR active agent is used with the CAR-modified immune cells than when the RAR/RXR active agent is not used with the CAR-modified immune cells or, similarly, that a given degree of effect can be obtained with a smaller dosage of CAR-modified immune cells when the RAR/RXR active agent is also used than would be required if the RAR/RXR active agent were not used.

As used herein, the term "potentiate" refers to an improved efficacy of CAR-modified immune cells, or improved response by the patient, when used in combination with a RAR/RXR active agent—especially an RARα antagonist, an RARγ agonist, an RXR antagonist, or combinations thereof—compared to the use of CAR-modified immune cells in the absence of the RAR/RXR active agent(s). As used herein, the term "augment" also refers to an improved effect when using an RAR/RXR active agent when compared to the situation where the RAR/RXR active agent is not used. The potentiation described herein arises from the immunoregulatory/immunomodulatory activity of the RAR/RXR active agent(s).

Multiple modes of potentiation are possible. In some modes the RAR/RXR active agent(s) acts directly on the CAR-modified immune cells. As delineated below, this can involve increasing the number or potency of effector cells and/or the suppression of Treg cells depending on the particular RAR/RXR active agent(s) used. These effects can be obtained by including the RAR/RXR active agent(s) in the preparatory cultures of the CAR-modified immune cells or by administering the RAR/RXR active agent(s) to the patient along with and/or subsequent to administration of the CAR-modified immune cells. In some modes the RAR/RXR active agent(s) act in conjunction with the CAR-modified immune cells by 1) modifying the tumor environment by reducing the presence or activity of Treg cells in the tumor thereby making the tumor more susceptible to immunologic attack, and/or 2) generating a pro-inflammatory response that acts on the CAR-modified immune cells to promote their effectiveness. These effects are generally dependent on the RAR/RXR active agent(s) being administered to the patient. Additionally, a general antitumor immune response in the patient promoted by RAR/RXR active agent(s) may further increase the overall effectiveness of these treatments.

Retinoic acid (RA), at higher pharmacological concentrations, causes anti-inflammatory effects by increasing levels of suppressive CD4$^+$ regulatory T cells (Treg cells). RA affects this function by enhancing expression of the transcription factor Fox P3 which is the master regulator of Treg cell differentiation. RA also reduces the levels of pro-inflammatory Th17 cells. RA elicits these effects by activating the RARα subtype of retinoic acid receptors. The above functions of RA or RARα selective agonists result in these compounds contributing to resistance of tumors to immunotherapy. The increased levels of suppressor Treg cells impede the anti-tumor activity of the T cells produced by immunotherapy. The complement of T cells attacking the tumor is also reduced by the RARα agonist since it reduces the levels of Th17 cells. Conversely, an antagonist of RARα sensitizes tumors to immunotherapy because the RARα antagonist reduces levels of the suppressive Treg cells and also increase levels of the effector Th17 cells. Thus, in one embodiment disclosed herein, a target cancer is treated with a combination of CAR-modified immune cells in combination with an RARα antagonist.

In another aspect of RA function, it has been shown that physiological concentrations of RA are critical for the development of T cell mediated immune responses. RA signaling to T cells is a critical early mediator of CD4$^+$ T cell effector function. Using T cells expressing dominant negative RARα (dnRARα), a modified RARα which abrogates RAR function, or a RAR antagonist, it was shown that RA signaling through RARα is required for T cell mediated functions such as skin graft rejection. Thus, in the context of cancer immunotherapy, use of RARα antagonists, or RARα inverse agonists, in combination with CAR-modified immune cells has counteracting effects: it can promote anti-tumor effects by decreasing levels of suppressive Treg cells, but such antagonists can also reduce anti-tumor effects by blocking CD4$^+$ T cell effector function. In this context, the use of RARα antagonists in combination with cancer immunotherapy may be of limited value and may even be detrimental.

In another embodiment disclosed herein, the RA signaling that is critical for the anti-cancer immune response is mediated by RARγ. In the above scenario, the sole use of RARα antagonists in conjunction with cancer immunotherapy will result only in a reduction of suppressor Treg cells and consequently in a limited enhancement of the anti-tumor effects of the immunotherapy. However, that approach does not take advantage of the early effects of RA or other RAR agonists acting through RARγ on promoting CD4$^+$ T cell effector function and the potential substantial enhancement of anti-tumor effects of co-administered cancer immunotherapy. Thus, RAR agonists which act specifically through RARγ will promote CD4$^+$ T cell effector function without increasing Treg cells and such RARγ selective agonists will substantially enhance the anti-tumor effects of cancer immunotherapy. In yet another embodiment, the cancer immunotherapy is used to treat a tumor together with a combination of a RARα antagonist and a RARγ agonist. In this situation, the retinoid compounds will enhance the anti-tumor activity of the immunotherapy by the following mechanisms: the RARγ agonist will facilitate the development of a robust CD4$^+$ T cell mediated immune response; the RARα antagonist will reduce the level of suppressor Treg cells and maintain the level of Th17 cells thereby minimizing modulation of the anti-tumor effects of the immunotherapy. It should be understood that the effect of using a RARα antagonist and a (non-selective) RAR agonist will be similar to using RARα antagonist and a RARγ agonist as the RARα antagonist will block the RARα agonistic activity of the (non-selective) RAR agonist.

RXR agonists promote the formation of suppressor Treg cells and inhibit the formation of effector Th17 cells. Thus in other embodiments, the use of a RXR antagonist (or inverse agonist) in combination with CAR-modified immune cells will enhance anti-tumor activity by decreasing formation of suppressor Treg cells and by increasing levels of Th17 effector cells.

In summary, the following classes of compounds will be useful in combination to increase the anti-tumor activity of cancer immunotherapy: RARα antagonists, RARγ agonists, and RXR antagonists. In the methods disclosed herein, CAR-modified immune cells are administered in combination with one or more of RAR/RXR active agents (for example, RARα antagonists, RARγ agonists, RXR antagonists), with or without other agents to treat certain cancers. The properties of RARα antagonism and RARγ agonism maybe present together in the same molecule. Thus, the same molecule acting as an antagonist at RARα can reduce Treg cell formation and, simultaneously, acting as an agonist at RARγ further reduce Treg cell formation and promote CD4$^+$ T cell effector function. In the same manner, the properties of RXR antagonism may be separately combined with the properties of RARα antagonism or RARγ agonism in distinct molecules. As used herein, the term "retinoid active agents" encompasses, without limitation, any compound acting on a RAR. Non-limiting examples of retinoid active agents are RARα antagonists and RARγ agonists. As used herein, the term "rexinoid active agents" encompasses, without limitation, any compound acting on a RXR. A non-limiting example of a rexinoid active agent is a RXR antagonist.

RAR/RXR active agents, as a class, and in many cases individually, are pleiotropic in effect. In the disclosed embodiments RAR/RXR active agents (for example, RARα antagonists, RARγ agonists, RXR antagonists) are used as immunotherapeutics or immunotherapeutic potentiators. This is an indirect mechanism of action in that the crucial effect is upon cells of the immune system rather than directly upon tumor cells. These or other RAR/RXR active agents may have other effects that may be useful in the treatment of some cancers by acting directly on the cancer cells either through a RAR/RXR-mediated mechanism (for example RXR antagonists) or through a non-RAR/RXR-mediated mechanism.

Cancer therapy can proceed through many mechanisms. Some anti-cancer agents are classified as anti-proliferative agents. These include the long-established chemotherapeutic agents which are generally cytotoxic as well as the more recently developed targeted therapies, such as kinase inhibitors which act upon growth regulating pathways in the cancer cells, and antibody-based therapeutics that recognize cell-surface antigens on the cancer cells. Other therapeutic modalities include anti-neovasculature, in which the in-growth of blood vessels into the tumor to supply it with nutrients is disrupted, and anti-hormonal in which hormone-dependent tumors are treated by disrupting hormonal supply or signaling.

It is also possible to distinguish between various modes of immunotherapy. For example one can distinguish between antibody-based therapies and cell-based therapies, and between passive and active therapies. As used herein passive therapy refers to a therapy in which the primary immunotherapeutic agent is administered to the patient. As used herein an active therapy refers to a therapy in which the primary immunotherapeutic agent is a component of an immune response induced in the patient by the administered agent, for example, a vaccine. Other immunotherapeutic agents are classified as immunomodulatory agents. As used herein the primary activity immunomodulatory agents is not direct therapeutic effect on the target disease, but rather increases or decreases the production or activity of immune system components that mediate or promote therapeutic effect. Such components of the immune system (cells or antibodies) act directly on the antigenic target or otherwise respond to antigenic stimulus to promote such a response, that is, in the currently disclosed embodiments, immune system components that act directly on tumor cells, particularly cancer cells, or provide helper function. Thus, in embodiments comprising administration of CAR-modified immune cells to a cancer patient, the CAR-modified immune cells are to be considered a passive, cellular immunotherapeutic. In a further aspect of these embodiments the CAR-modified immune cells have direct cytotoxic effect. In embodiments involving use of RAR/RXR active agents, whether in CAR-modified immune cell culture or administered to a cancer patient, the RAR/RXR active agents are to be considered immunomodulatory agents. Similarly, in those embodiments involving administration of an immune checkpoint inhibitor, the immune checkpoint inhibitor is to be considered an immunomodulatory agent, even if the immune checkpoint inhibitor is an antibody.

Various embodiments are directed exclusively to an immunotherapeutic mechanism, that is, the RAR/RXR active agents are used promote an immunological attack on the tumor, and other activities the RAR/RXR active agents may possess, if any, are not crucial to effectiveness. Some embodiments may exclude agents possessing other anticancer activities. Other embodiments may take advantage of additional activities of the RAR/RXR active agent(s). Similarly, some embodiments entail administration of only the RAR/RXR active agent(s) and the CAR-modified immune cells. Other embodiments are permissive of combination with other therapies and therapeutic agents. Some of these embodiments specifically include one or another of the other therapies and therapeutic agents. Others or these embodiments specifically exclude one or another of the other therapies and therapeutic agents. Other therapies or therapeutic agents include other immunotherapies, anti-proliferative therapy, chemotherapy, cytotoxic agents, cytostatic agents, targeted therapy, radiation therapy, anti-hormonal therapy, anti-neovasculature therapy, anti-tumor antigen antibodies, anti-cancer vaccines, immune checkpoint inhibitors, and immune checkpoint inhibitor antibodies. Thus, for example, some embodiments specifically include or exclude use of immune checkpoint inhibitors, or permit combination with immune checkpoint inhibitors, but exclude other immunotherapeutics or other cancer therapies.

The term "agonist" as used herein shall be understood to mean a compound which binds to a receptor and activates it, producing gene transcription and a subsequent pharmacological response (e.g., contraction, relaxation, secretion, enzyme activation, etc.). As used herein, the term "RARγ agonist" refers to a compound that binds to RARγ with a higher affinity compared to binding with another molecule, such as a different RAR. In exemplary embodiments, a RARγ agonist is selective for RARγ over RARα and/or RARβ. Thus, a RAR selective agonist tends to bind to a particular RAR receptor target with high binding affinity. As used herein, the term "agonist" includes selective agonists.

The term "antagonist" as used herein, refers to a compound that attenuates the effect of an agonist by binding in the same site as an agonist without activating the receptor. An antagonist by itself will not affect the gene transcriptional activity of the unoccupied receptor. Conventionally, a RARα antagonist is a chemical agent that inhibits the activity of an RARα agonist. As used herein, the term "RXR antagonist" refers to compounds that bind to RXR and do not activate it, but instead antagonize transcription produced by a RXR agonist. As used herein, the term "antagonist" includes selective antagonists.

The term "inverse agonist" as used herein shall be understood to mean a compound which produces an effect opposite to that of an agonist, yet acts at the same receptor. An inverse agonist by itself will reduce the basal gene transcriptional activity of the unoccupied receptor.

RARα Antagonists

In certain embodiments, the RARα selective antagonist is a compound represented by the general formula (I):

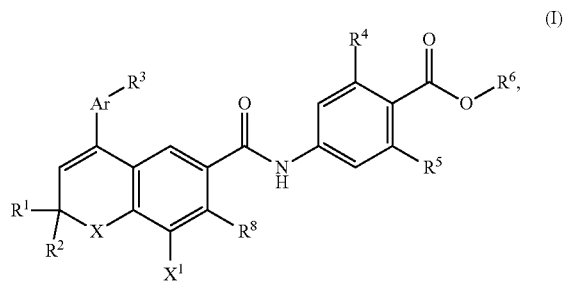

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH. Each combination of R groups and each combination of their independently selected substituents defines a distinct individual embodiment.

An exemplary RARα selective antagonist of the general formula (I) is the compound AGN194301:

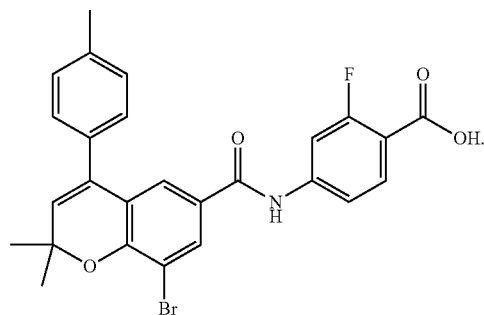

Other exemplary RARα antagonists of the general class of general formula (I) include, but are not limited to, AGN193491, AGN193618, AGN194202, AGN193625, and AGN194574.

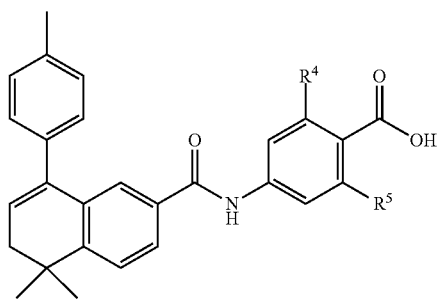

R⁴ and R⁵ both H; AGN 193491
R⁴ = F, R⁵ = H; AGN193618
R⁴ and R⁵ both F; AGN194202

AGN 194574

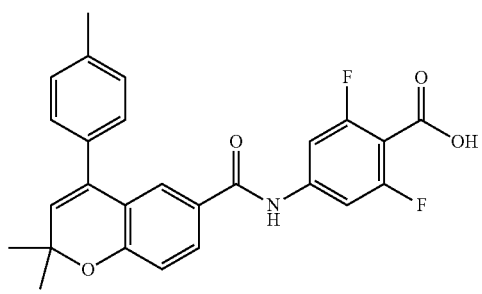

In other embodiments, the RARα selective antagonist is a member of the class of compounds represented by general formula (II)

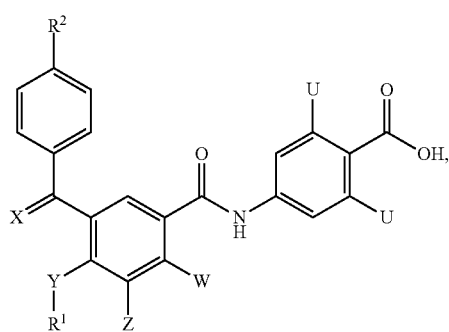

(II)

wherein $R^1$ and $R^2$ are independently $C_{1-6}$ alkyl; X is O, S, or CH$_2$; Y is O, S, CH$_2$, or NR$^3$, wherein $R^3$ is $C_{1-6}$ alkyl; Z is Cl or Br; W is H or OH; and U is independently H or F. Each combination of R groups and each combination of their independently selected substituents defines a distinct individual embodiment.

An exemplary RARα selective antagonist of the class represented by general formula (II) for use in the methods disclosed herein is represented by the following structure (VTP196696):

VTP 196696

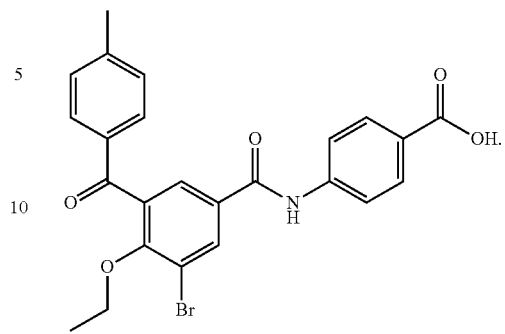

In other embodiments, RARα selective antagonists are compounds of the general formula (III).

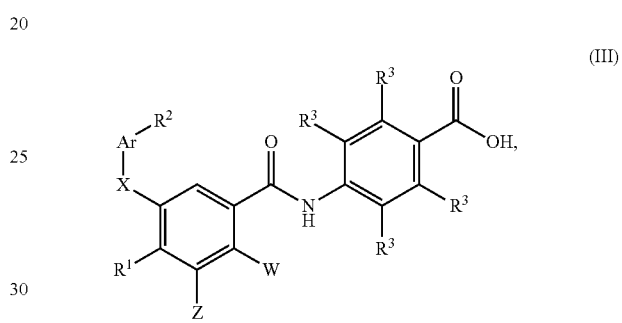

(III)

wherein $R^1$ and $R^2$ are independently H or $C_{1-6}$ alkyl; $R^3$ is H or F; Ar is phenyl, pyridyl, thienyl, furyl, or naphthyl; X is O, S, N, or CH$_2$; W is H or OH; and Z is Cl or Br. Each combination of R groups and each combination of their independently selected substituents defines a distinct individual embodiment.

An exemplary compound of general formula (III) is AGN194777.

AGN 194777

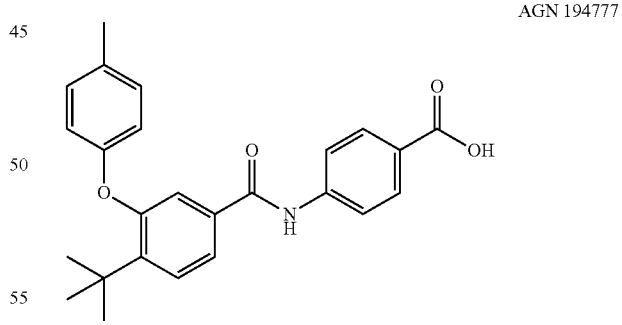

Other exemplary RARα antagonists include, but are not limited to, BMS185411, BMS614, Ro41-5253, and Ro46-5471.

Additional RAR antagonists or inverse agonists are described in U.S. Pat. Nos. 6,037,488, 5,612,356, 5,776,699, 5,958,954, 5,877,207, 6,225,494, 6,455,701, 5,723,666, 5,739,338, and 5,919,970, and US Patent Application 2009/0176862, all of which are incorporated by reference herein for all they disclose of RAR antagonists.

RARγ Agonists

Exemplary RARγ agonists are disclosed in U.S. Pat. Nos. 5,234,926, 4,326,055, 5,324,840, 5,824,685, and 6,452,032, including but not limited to the following compounds.

AGN 190183

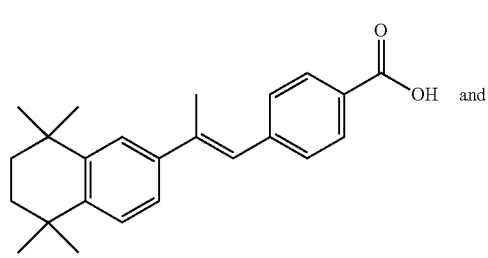

and

AGN 190205

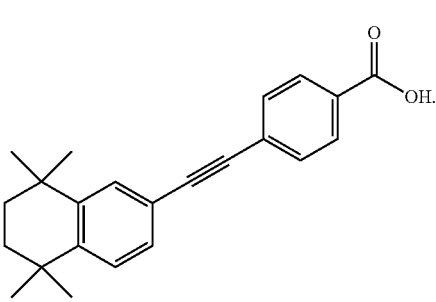

Another exemplary RARγ agonist is AGN 190168.

AGN 190168

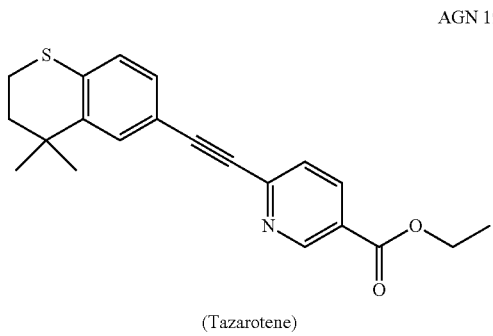

(Tazarotene)

Although compounds such as AGN190183, AGN190205, AGN190168 (tazarotene) are RARγ agonists they are not RARγ selective since they activate RARα and/or RARβ as well. It may be preferable to use RARγ selective agonists since activation of RARα may negate the T effector cell activation effects produced by RARγ activation by increasing production of Treg cells. RARγ selective agonists, on the other hand, will potentiate the anti-tumor effects of cancer immunotherapeutics.

An example of a highly selective RARγ agonist is the compound:

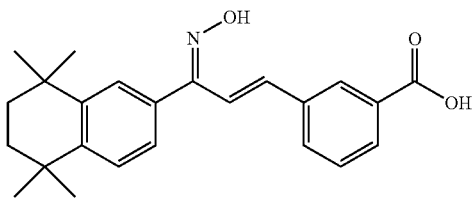 [SMILES: CC1(C)CCC(C)(C)c2cc(C(/C=C/c3cccc(C(=O)O)c3)=N/O)ccc21]

Other RARγ selective agonists are members of the family of compounds of general formula (IV):

(IV)

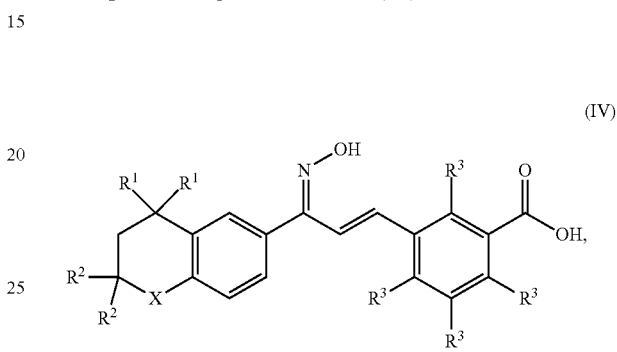

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl. Each combination of R groups and each combination of their independently selected substituents defines a distinct individual embodiment.

Additional RARγ selective agonists include, but are not limited to, CD437, CD2325, CD666, and BMS961. Additional RARγ agonists are described in International Publication WO 02/28810A2 which is incorporated by reference herein for all it discloses regarding RARγ agonists.

RXR Antagonists

Exemplary RXR antagonists include, but are not limited to, AGN195393, LGN100849, HX531, LG100754, PA451, PA452, and UVI 3003.

HX 531

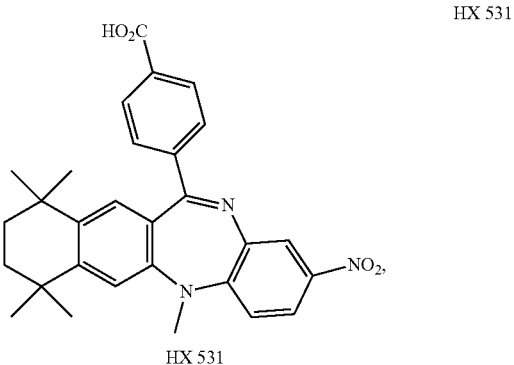

HX 531

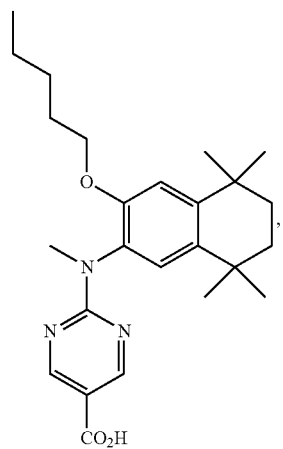

PA 451

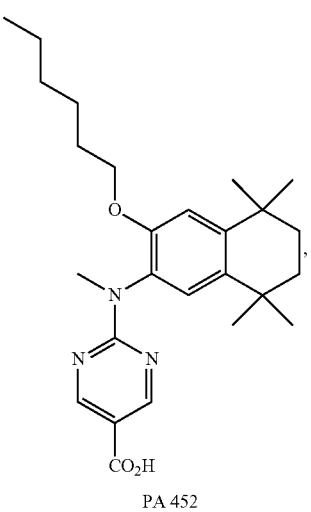

PA 452

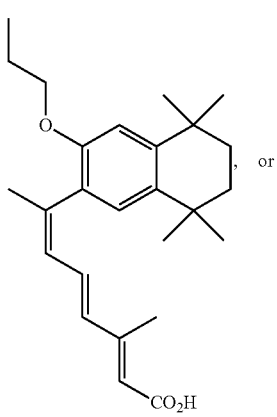

or

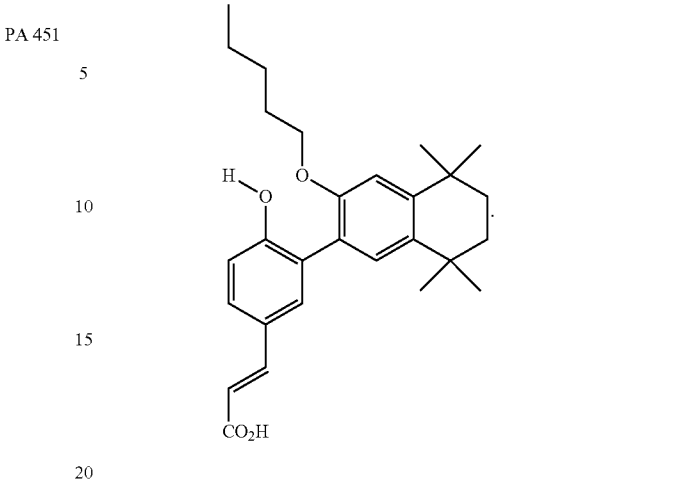

PA 451

PA 452

LG 100754

UVI 3003

CAR-Modified Immune Cells

Tumor cells often down-regulate major histocompatibility complex (MHC) expression and furthermore, when they do express MHC alleles, the immunodominant epitopes are not often known. Thus, MHC-dependent cancer immunotherapies are often not effective. Chimeric antigen receptor (CAR)-modified immune cells react with target antigens on cancer cells in an MHC-independent matter. The CAR allows binding via the antigen-binding domain to a target cells wherein the CAR-modified cells kill the target cells in a MHC non-restricted manner by binding to the target cells and induction of activation, proliferation, and cytotoxicity of the modified cells against the tumor target.

As used herein, the term "target cells" refers to cells expressing a surface antigen that can be bound by the CAR. The antigen can also be referred to as the "target antigen." Target antigens are antigens that are differentially expressed on cancer cells such that the CAR targets the cancer cells preferentially over non-cancer cells.

Once the modified immune cells bind to target antigen, the internal stimulatory domains provide the necessary signals for the immune cell to become fully active. In this fully active state, the immune cells can more effectively proliferate and attack cancer cells.

CAR-modified cells can recognize a variety of types of antigen, not only protein but also carbohydrate and glycolipid structures typically expressed on the tumor cell surface. Unlike T cell receptor (TCR) recognition, the antigen does not need to be processed and presented by MHC and therefore the same CAR-molecule can be used in all patients who express the same tumor antigen regardless of HLA type.

The CAR comprises a recombinant polypeptide construct comprising at least an antigen-binding domain, a transmembrane domain, and one or more intracellular stimulatory domains (also referred to as a cytoplasmic signaling domain or an intracellular signaling domain). The antigen-binding domain allows the modified immune cells to specifically bind to the target tissue, the transmembrane domain anchor the CAR to the immune cells, and the intracellular stimulatory domain induces persistence, trafficking, and effector functions in the transduced cells.

The antigen-binding domain of a CAR is often derived from a monoclonal antibody, but other ligands (e.g., heregulin, cytokines) and receptors (e.g., NKp30) can also be used. The antigen-binding domain can include any fragment of an antibody that retains antigen-binding function. For example, the CAR antigen-binding domain is often contributed by a single-chain variable fragment (scFv), which is formed from the variable regions of heavy and light chains of a monoclonal antibody.

In one aspect, the transmembrane domain comprises a sequence of the zeta (ζ) chain associated with the T cell receptor complex, such as the intracellular domain of human CD3 ζ chain.

The intracellular stimulatory domain can include one or more of CD28, 4-1BB (CD137), CD134 (OX-40), ICOS, and CD40L.

The antigen-binding domain, transmembrane domain, and the intracellular stimulatory domain(s) are linked either directly or via a spacer sequence.

The CAR sequences are incorporated in an expression vector. Various expression vectors are known in the art and any such vector may be utilized. In some embodiments, the vector will be a retroviral or lentiviral vector. In other embodiments the vector will be derived from adeno-associated virus.

Immune cells are transformed with the CAR and the CAR is then expressed on the cell surface. Typically, the immune cell stably expresses the CAR, although in some embodiments, the immune cell may transiently express the CAR. The immune cell is thus transfected with a nucleic acid, e.g., mRNA, cDNA, DNA, encoding a CAR. Immune cells of the disclosure include mammalian cells (e.g., human cells), and can be autologous cells, syngeneic cells, allogenic cells and even in some cases, xenogeneic cells, The cells are engineered to express a CAR and, therefore, are not found in nature. Exemplary immune cells include T lymphocytes (T cells), natural killer (NK) cells, NKT cells, and macrophages (including monocytes and dendritic cells).

The CAR-modified immune cells are then cultured to expand the populations obtain a suitable number of cells for a single dose or for multiple doses. In certain embodiments, one or more retinoid and/or rexinoid active agents are added to the expansion cultures during the culture period and have an effect on the CAR-modified cells directly. For example, in culturing CAR-MIC the one or more retinoid and/or rexinoid active agents added to the expansion cultures would be chosen for their ability to, for example, suppress the development of Treg cells and/or their ability to promote the development Th17 cells. In some embodiments, the one or more retinoid and/or rexinoid active agents are included in the expansion culture of CAR-modified immune cells and administered directly to a subject.

Immune Checkpoint Targeted Cancer Therapeutics

Immune checkpoint therapy targets regulatory pathways in the differentiation and activation of T cells to promote the passage of T cell developmental program through these checkpoints so that anti-tumor (or other therapeutic) activity can be realized. The agents bringing about immune checkpoint therapy are commonly called immune checkpoint inhibitors and it should be understood that it is the check on T cell development that is being inhibited. Thus, while many immune checkpoint inhibitors also inhibit the interaction of receptor-ligand pairs (e.g., anti-PD-1, anti-PD-L1, and CTLA-4), others (such as anti-OX40 and anti-ICOS) act as agonists of targets that release or otherwise inhibit the check on T cell development, ultimately promoting effector function and/or inhibiting regulatory function.

Disclosed herein is the use of retinoid and rexinoid receptor active molecules (RAR/RXR active agents) as potentiators of the anti-tumor effects of immune checkpoint inhibitor molecules in combination with CAR-modified immune cells. Molecules which inhibit immune checkpoint proteins include antibodies which are specific to one or more of PD-1, PD-1 ligand, CTLA-4, TIM-3, LAG-3, B7-H3, and B7-H4.

Programmed death-1 (PD-1) is a checkpoint protein on T cells and normally acts as a type of "off switch" that helps keep the T cells from attacking other cells in the body. It does this by binding to programmed death ligand-1 (PD-L1), a protein on some normal and cancer cells. When PD-1 binds to PD-L1, the T cells will not attack the target cells. Some cancer cells have large amounts of PD-L1, which helps them evade immune attack. Monoclonal antibodies that target either PD-1 or PD-L1 can boost the immune response against cancer cells and have shown a great deal of promise in treating certain cancers. Examples of monoclonal antibodies that target PD-1/PL-L1 include: the anti-PD-1 mAbs nivolumab (OPDIVO®, Bristol-Myers Squibb) and pembrolizumab (KEYTRUDA®, Merck & Co.), BMS-936559 (Bristol-Myers Squibb), pidilizumab (Medivation): and the anti-PD-L1 mAbs durvalumab (MED14736, IMFINZI™, Medimmune), atezolizumab (MPDL3280A; TECENTRIQ®, Hoffman-La Roche), avelumab (BAVENCIO®, EMD Serono). These antibodies have, variously, demonstrated utility in treating a variety of cancers including malignant melanoma (MM), renal cell carcinoma (RCC), Merkel cell carcinoma, urothelial carcinoma, and non-small cell lung cancer (NSCLC). Non-antibody inhibitors of PD-1/PD-I1 interaction are also being developed; for example, small engineered proteins based on stefin A (called AFFIMER® molecules). In addition to PD-L1, PD-1 can also bind to PD-L2. In addition to PD-1, PD-L1 can also bind to B7-1 (CD80).

CTLA-4 is an immune checkpoint molecule expressed on the surface of CD4 and CD8 T cells and on CD25+, FOXP3+ T regulatory (Treg) cells. CTLA-4 generates inhibitory signals that block T cell responses and enables tumor growth. Anti-CTLA-4 mAbs such as ipilimumab (YERVOY®; Bristol-Myers Squibb) cause shrinkage of tumors in animal models. Ipilimumab improves overall survival in MM patients and is approved for the treatment of MM. Responses have been observed in RCC and NSCLC as well. Other exemplary anti-CTLA-4 antibodies include tremelimumab (Medimmune).

The CTLA-4-blocking antibody ipilimumab gives durable responses only in a subset of melanoma patients and its effects on overall survival is limited. This has led to the search for resistance mechanisms to CTLA-4 blockade and to the identification of the cytosolic enzyme indoleamine 2,3-dioxygenase (IDO) as a potent mediator of melanoma resistance. IDO directly suppresses effector T cells and activates suppressive Treg cells thereby modulating the anti-tumor effects of CTLA-4 blockade. Inhibitors of IDO such as 1-methyl-tryptophan have T cell dependent anti-tumor effects and synergize with CTLA-4-blocking antibody to control tumor growth and enhance survival.

TIM-3 (T-cell immunoglobulin and mucin-domain containing-3) is a molecule selectively expressed on IFN-γ-producing $CD4^+$ T helper 1 (Th1) and $CD8^+$ T cytotoxic 1 (Tc1) T cells. TIM-3 is an immune checkpoint receptor that functions specifically to limit the duration and magnitude of Th1 and Tc1 T-cell responses. Exemplary antibodies to TIM-3 are disclosed in U.S. Patent Application Publication 20160075783 which is incorporated by reference herein for all it contains regarding anti-TIM-3 antibodies.

LAG-3 (lymphocyte-activation gene 3; CD223) negatively regulates cellular proliferation, activation, and homeostasis of T cells, in a similar fashion to CTLA-4 and PD-1 and plays a role in Treg suppressive function. Exemplary antibodies to LAG-3 include GSK2831781 (GlaxoSmithKline), BMS-986016 (Bristol-Myers Squibb) and the antibodies disclosed in U.S. Patent Application Publication 2011/0150892 which is incorporated by reference herein for all it contains regarding anti-LAG-3 antibodies.

The B7 family is a family of costimulatory proteins which are expressed on the surface of antigen-presenting cells and interact with ligands on T cells. B7-H3 (CD276) is one of the molecules in this family. An antibody to B7-H3, enoblituzumab (EMPLICITI™, Bristol-Myers Squibb) is approved for treatment of multiple myeloma. Another molecule in the family is B7-H4 (V-set domain-containing T-cell activation inhibitor 1), antibodies against which are in development.

Other immune checkpoint inhibitor targets, B- and T-cell attenuator (BTLA), inducible T-cell costimulator (ICOS), OX40 (tumor necrosis factor receptor superfamily, member 4), and others are potentially useful in the disclosed methods. Several anti-OX40 agonistic monoclonal antibodies are in early phase cancer clinical trials including MED10562 and MED16469 (Medimmune), MOXR0916 (Genentech), and PF-04518600 (Pfizer); as is an anti-ICOS agonistic antibody, JTX-2011 (Jounce Therapeutics).

Disclosed herein are methods of potentiating the anticancer activity of immune checkpoint targeting immunotherapeutics including a CTLA-4 inhibitor, a PD-1 inhibitor, a TIM-3 inhibitor, a LAG-3 inhibitor, a PD-1 ligand (such as PDL-1), an inhibitor of a PD-1 ligand, an OX40 agonist, an ICOS agonist, a B7-H3 protein, an inhibitor of a B7-H3 protein, a B7-H4 protein, and an inhibitor of a B7-H4 protein. In certain embodiments, the inhibitors are antibodies.

The immune checkpoint targeting immunotherapeutic antibodies can be whole antibodies or antibody fragments. The terms "fragment of an antibody," "antibody fragment," and "functional fragment of an antibody" are used interchangeably herein to mean one or more fragments of an antibody that retain the ability to specifically bind to an antigen. The antibody fragment desirably comprises, for example, one or more complementary determining regions (CDRs), the variable region (or portions thereof), the constant region (or portions thereof), or combinations thereof. Examples of antibody fragments include, but are not limited to, a Fab fragment, which is a monovalent fragment consisting of the $V_L$, $V_H$, $C_L$, and $CH_1$ domains; a $F(ab')_2$ fragment, which is a bivalent fragment comprising two Fab fragments linked by a disulfide bridge at the hinge region; a Fv fragment consisting of the $V_L$ and $V_H$ domains of a single arm of an antibody; a single chain Fv, in which the $V_L$ and $V_H$ domains are joined by a peptide linker sequence; a Fab' fragment, which results from breaking the disulfide bridge of an $F(ab')_2$ fragment using mild reducing conditions; a disulfide-stabilized Fv fragment (dsFv); and a domain antibody (dAb), which is an antibody single variable region domain (VH or VL) polypeptide that specifically binds antigen. It should also be realized that any of these forms of antigen-binding antibody fragments can provide the antigen binding domain of a CAR.

In alternative embodiments the antibody is replaced with another protein that similarly binds to the immune checkpoint target molecule. In some instances these non-antibody molecules comprise an extracellular portion of the immune checkpoint target molecule's ligand or binding partner, that is, at least the extracellular portion needed to mediate binding to the immune checkpoint target molecule. In some embodiments this extracellular binding portion of the ligand is joined to additional polypeptide in a fusion protein. In some embodiments the additional polypeptide comprises an Fc or constant region of an antibody.

Methods of Treatment

Provided herein are methods of treating cancer in a mammal by administering CAR-modified immune cells and one or more RAR/RXR active agents. More specifically these are methods of cancer immunotherapy and methods of potentiating CAR-modified immune cell immunotherapy. In some embodiments, immune checkpoint inhibitors are administered in addition to the CAR-modified immune cells and one or more RAR/RXR active agents. Also provided are methods of decreasing tumor burden, increasing the disease-free survival in subject with cancer. Other embodiments relate to compositions comprising such agents for use in the treatment of cancer, in cancer immunotherapy, and in potentiating CAR-modified immune cell-mediated immunotherapy. Still other embodiments relate to compositions for use in making medicaments for the treatment of cancer, for cancer immunotherapy, and for potentiating CAR-modified immune cell-mediated immunotherapy. It is to be understood that the multiple agents used may be provided in separate compositions or medicaments which may be administered by separate routes of administration and/or at separate times; nonetheless use of such multiple compositions or medicaments is coordinated so that the patient to whom they are administered receives the benefit of the combined, interacting activity of the multiple agents. For each method of treating cancer disclosed herein there are corresponding methods of cancer immunotherapy. For each method of treating cancer or cancer immunotherapy there are corresponding methods of potentiating cancer treatment/immunotherapy.

In some embodiments, the method comprises administering CAR-modified immune cells and an RAR active agent. In some embodiments, the method comprises administering CAR-modified immune cells and an RARα antagonist. In some embodiments, the method comprises administering CAR-modified immune cells and an RARγ agonist. In some embodiments, the method comprises administering CAR-modified immune cells and two RAR active agents. In some embodiments, the method comprises administering CAR-modified immune cells and an RARα antagonist an RAR agonist. In some embodiments, the method comprises administering CAR-modified immune cells and an RARα antagonist an RARγ selective agonist. In certain embodiments, the RARα antagonist is AGN194301, AGN193491, AGN193618, AGN194202, AGN194574, VTP196696, AGN19477, BMS185411, BMS614, Ro41-5253, or Ro46-5471. In some embodiments the RAR agonist is AGN190183, AGN190205, AGN204647, or tazarotene. In some embodiments, the RARγ selective agonist is CD437, CD2325, CD666, or BMS961.

In some embodiments, the method comprises administering CAR-modified immune cells and an RXR active agent. In some embodiments, the method comprises administering CAR-modified immune cells and an RXR antagonist. In some embodiments, the RXR antagonist is AGN195393 or LGN100849. With respect to the use of multiple RAR/RXR active agents in the various use or method of treatment embodiments described herein, any of the disclosed general formula genera, sub-genera thereof, and individual species may be combined with any other general formula genera, sub-genera thereof, and individual species, each such combination defining an individual embodiment.

The compounds, pharmaceutical compositions, and methods disclosed herein are particularly useful for the treatment of cancer. As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes, but is not limited to, solid tumors and hematologic tumors. The term "cancer" encompasses diseases of skin, tissues, organs, bone, cartilage, blood, and vessels. The term "cancer" further encompasses primary and metastatic cancers. Included within the term "cancer cells" are cancer stem cells.

The disclosed methods can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, a hematologic cancer, or Merkel cell carcinoma. In some embodiments, the hematologic cancer is a leukemia, a lymphoma, a myelodysplastic syndrome, or a myeloma. In select embodiments a particular type of cancer is treated. In other select embodiments a particular type of cancer is excluded from treatment.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the CAR-modified immune cells and one or more retinoid and/or rexinoid active agents to elicit a desired response in the individual. For example, a therapeutically effective amount of a retinoid-active agent disclosed herein is an amount which potentiates the anti-cancer activity of CAR-modified immune cells or leads to an increase in occurrence or duration of disease-free survival in a subject.

Additionally, one or more retinoid and/or rexinoid active agents can decrease toxicity associated with CAR-modified immune cells by allowing a lower dose of CAR-modified immune cells to be administered with the same efficacy or a higher dose of the CAR-modified immune cells can be administered with the same degree of safety.

The term "treating" or "treatment" broadly includes any kind of treatment activity, including the diagnosis, mitigation, or prevention of disease in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

A typical dose of CAR-modified immune cells can be, for example, in the range of $1 \times 10^6$ to $3 \times 10^{10}$ cells per dose. In some embodiments, CAR-modified immune cells are administered at a dose of at least $1 \times 10^6$ cells/dose, at least $3 \times 10^6$ cells/dose, at least $1 \times 10^7$ cells/dose, at least $3 \times 10^7$ cells/dose, at least $1 \times 10^8$ cells/dose, at least $3 \times 10^8$ cells/dose, at least $1 \times 10^9$ cells/dose, at least $3 \times 10^9$ cells/dose, at least $1 \times 10^{10}$ cells/dose, at least $3 \times 10^{10}$ cells/dose, or a range defined by any two of the foregoing values. In some embodiments, the typical dose of CAR-modified immune cells can be, for example, in the range of $1 \times 10^5$ to $1 \times 10^8$ cells per kilogram of patient body weight. In some embodiments, CAR-modified immune cells are administered at a dose of at least $1 \times 10^5$ cells/kg, at least $3 \times 10^5$ cells/kg, at least $6 \times 10^5$ cells/kg, at least $1 \times 10^6$ cells/kg, at least $3 \times 10^6$ cells/kg, at least $6 \times 10^6$ cells/kg, at least $1 \times 10^7$ cells/kg, at least $3 \times 10^7$ cells/kg, or a range defined by any two of the foregoing values.

Therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the present disclosure. The desired dosage can be delivered by a single bolus administration, by multiple bolus administrations, or by continuous infusion administration of the CAR-modified immune cells. In various embodiments the continuous infusion may extend for half an hour, for an hour, for several hours, for a day, or for several days. Treatment may comprise a single or multiple infusions.

In some embodiments, the CAR-modified immune cells are administered with other pre-treatment or simultaneous administrations of additional agents. In some embodiments, subjects who are to receive CAR-modified immune cells are pre-treated with a non-myeloablative lymphocyte-depleting regiment, such as, but not limited to, treatment with cyclophosphamide and/or fludarabine. In some embodiments, CAR-modified immune cells are administered with interleukin-2.

CAR-modified immune cells may be administered to a subject a single time or multiple times. The cells can be administered weekly, biweekly, monthly, bimonthly, or upon evidence of cancer progression.

Depending on the type of cancer, and the patient to be treated, as well as the route of administration, the disclosed RARα antagonists, RARγ agonists and RXR antagonists may be administered at varying therapeutically effective doses to a patient in need thereof.

However, the dose administered to a mammal, particularly a human, in the context of the present methods, should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Typical doses of RARα antagonists are 0.01 to 300 mg/m²/day; however, doses below or above this exemplary range are within the scope of the present disclosure. The daily dose can be about 0.5 to 100 mg/m²/day, 1 to 90 mg/m²/day, 5 to 80 mg/m²/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m²/day; or not more than 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m²/day; or a range defined by any two of the foregoing values.

Typical doses of RARγ agonists are 0.01 to 300 mg/m²/day; however, doses below or above this exemplary range are within the scope of the present disclosure. The daily dose can be about 0.5 to 100 mg/m²/day, 1 to 90 mg/m²/day, 5 to 80 mg/m²/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m²/day; or not more than 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m²/day; or a range defined by any two of the foregoing values.

Typical doses of RXR antagonists are 0.01 to 300 mg/m²/day; however, doses below or above this exemplary range are within the scope of the present disclosure. The daily dose can be about 0.5 to 100 mg/m²/day, 1 to 90 mg/m²/day, 5 to 80 mg/m²/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m²/day; or not more than 0.1, 0.2, 0.3, 0.5, 0.7, 1, 2, 3, 5, 7, 10, 15, 20, 25, 30, 50, 60, 70, 80, 90, 100, 125, 150, 175, 200, 225, 250, 275, or 300 mg/m²/day, or a range defined by any two of the foregoing values.

The average surface area of a human body is generally accepted to be 1.9 m² for an adult male, 1.6 m² for an adult female, and 1.33 m² for a 12-13 year old child. These values can be used to calculate dose ranges for daily dosage for the values in the preceding paragraphs. The total daily dosage of RAR/RXR active agents can be administered as a single dose or as two doses administered with a 24 hour period spaced 8 to 16, or 10 to 14, hours apart. The RAR/RXR active agents are administered in coordination with the CAR-modified immune cells and as above therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the disclosure. The desired dosage can be delivered by a single bolus administration of the composition, by multiple bolus administrations of the composition, or by continuous infusion administration of the composition.

The retinoid and/or rexinoid active agent can be administered to a mammal using standard administration techniques, including parenteral, oral, intravenous, intraperitoneal, subcutaneous, pulmonary, transdermal, intramuscular, intranasal, buccal, sublingual, or suppository administration. The term "parenteral," as used herein, includes intravenous, intramuscular, subcutaneous, rectal, vaginal, and intraperitoneal administration. The CAR-modified immune cells are administered to a mammal using peripheral systemic delivery by intravenous, intraperitoneal, or subcutaneous injection. The retinoid and/or rexinoid active agent preferably is suitable for oral administration, for example as a pill, tablet or capsule.

Administration may be continuous or intermittent. The dosage may also be determined by the timing and frequency of administration. Thus, the RARα agonists disclosed herein can be given on a daily, weekly, biweekly, or monthly basis for a period of time, followed by an optional drug holiday (drug free period) and that this drug administration/drug holiday cycle can be repeated as necessary. In certain embodiments, the total daily dosage of RARα agonists can be administered as a single dose or as two doses administered with a 24 hour period spaced 8 to 16, or 10 to 14, hours apart.

The CAR-modified immune cells and retinoid and/or rexinoid active agents disclosed herein may be administered at substantially the same time (within 1 hr. of each other) or at different times. In some embodiments, the subject is pre-treated with a retinoid and/or rexinoid active agent at least 30 min, at least 1 hr., or at least 2 hrs. before administration of the CAR-modified immune cells. In preferred embodiments, the subject is pretreated with a retinoid and/or rexinoid active agent for at least 12 hours, or 1 day, 2, 3, 4, 5 days prior to administration of the CAR-modified immune cells. In some embodiments, the subject is pretreated with a retinoid and/or rexinoid active agent for 5-10 days, for example 6, 7, or 8 days, prior to administration of the CAR-modified immune cells; or for any range defined by any of two the foregoing values. In some embodiments, the retinoid and/or rexinoid active agent is administered after the onset of CAR-modified immune cells administration, for example, the same day, the next day, two days later, three days later, a week later, etc. It is anticipated that RAR/RXR therapy will be administered on a daily basis for a period of time and may be given longer than CAR-modified immune cells. In some embodiments administration the RAR and/or RXR active agent(s) continues until such time as the patient has demonstrated a durable complete response (that is, a complete response for at least 6 months following administration of the CAR-modified immune cells). In other embodiments, administration of the RAR and/or RXR active agent(s) continues for as long as tumor regression proceeds or there is stable disease.

The CAR-modified immune cells and retinoid and/or rexinoid active agents disclosed herein may be administered in combination with other drugs, such as at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. In other embodiments the CAR-modified immune cells and retinoid and/or rexinoid active agents are the only therapeutic reagents administered or the only treatment given; or the only treatment or reagents given, the primary utility of which is to promote an anti-cancer immune response.

The effectiveness of cancer therapy is typically measured in terms of "response." The techniques to monitor responses can be similar to the tests used to diagnose cancer such as, but not limited to:

A lump or tumor involving some lymph nodes can be felt and measured externally by physical examination.

Some internal cancer tumors will show up on an x-ray or CT scan and can be measured with a ruler.

Blood tests, including those that measure organ function can be performed.

A tumor marker test can be done for certain cancers.

Regardless of the test used, whether blood test, cell count, or tumor marker test, it is repeated at specific intervals so that the results can be compared to earlier tests of the same type.

Response to cancer treatment is defined several ways:

Complete response—all of the cancer or tumor disappears; there is no evidence of disease. Expression level of tumor marker (if applicable) may fall within the normal range.

Partial response—the cancer has shrunk by a percentage but disease remains. Levels of a tumor marker (if applicable) may have fallen (or increased, based on the tumor marker, as an indication of decreased tumor burden) but evidence of disease remains.

Stable disease—the cancer has neither grown nor shrunk; the amount of disease has not changed. A tumor marker (if applicable) has not changed significantly.

Disease progression—the cancer has grown; there is more disease now than before treatment. A tumor marker test (if applicable) shows that a tumor marker has risen.

Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis.

In some embodiments of the current method, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 1-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 5-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 10-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In yet other embodiments, the subject has a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more.

In other embodiments, the method may help to treat or alleviate conditions, symptoms, or disorders related to cancer. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss. In other embodiments, the administration of both the RARα agonist and CAR-modified immune cells prolongs the survival of the individual being treated relative to treatment with the CAR-modified immune cells alone.

LIST OF PARTICULAR EMBODIMENTS

The following listing of embodiments is illustrative of the variety of embodiments with respect to breadth, combinations and sub-combinations, class of invention, etc., elucidated herein, but is not intended to be an exhaustive enumeration of all embodiments finding support herein.

Embodiment 1

A method of cancer immunotherapy comprising administering to a subject in need thereof chimeric antigen receptor-modified immune cells (CAR-MIC) and at least one retinoid active agent and/or rexinoid active agent (RAR/RXR active agent).

Embodiment 2

A method of treating cancer comprising administering to a subject in need thereof (CAR-MIC) and at least one RAR/RXR active agent.

Embodiment 3

A method of potentiating CAR-MIC cancer immunotherapy comprising administering at least one RAR/RXR active agent to a cancer patient who is receiving, has received, or is scheduled to receive CAR-MIC.

Embodiment 4

A method of cancer immunotherapy comprising administering to a subject in need thereof CAR-MIC, wherein the CAR-MIC are cultured in a culture medium comprising at least one RAR/RXR active agent prior to being administered to the subject.

Embodiment 5

A method of prolonging the disease-free survival of a cancer patient comprising administering CAR-MIC and at least one RAR/RXR active agent.

Embodiment 6

A method of decreasing toxicity of CAR-MIC comprising administering to a subject in need thereof at least one RAR/RXR active agent in combination with the CAR-MIC such that as a result of the combination, a lower dose of CAR-MIC are administered with greater safety and equal efficacy than if the CAR-MIC were administered alone; or alternatively allowing equally safe administration of a higher dose of CAR-MIC with greater efficacy.

Embodiment 7

A method of expanding the number of CAR-MIC in vitro comprising culturing the CAR-MIC in a culture medium comprising at least one RAR/RXR active agent.

Embodiment 8

The method of any one of Embodiments 1-6, wherein the CAR-MIC are cultured in a culture medium comprising at least one RAR/RXR active agent prior to being administered to the subject.

Embodiment 9

The method of any one of Embodiments 1-8, wherein the at least one RAR/RXR active agent is a RARα antagonist, a RARγ agonist, a RXR antagonist, or a combination thereof.

Embodiment 10

The method of any one of Embodiments 1-6 or 8-9, further comprising administration of an immune checkpoint inhibitor.

Embodiment 11

The method of Embodiment 10 wherein the immune checkpoint inhibitor is an inhibitor of at least one of CTLA-4, PD-1, TIM-3, LAG-3, PD-L1 ligand, B7-H3, B7-H4, BTLA, or is an ICOS, or OX40 agonist.

Embodiment 12

The method of Embodiment 10 or 11, wherein the immune checkpoint inhibitor is an antibody.

Embodiment 13

The method of any one of Embodiments 1-12, wherein the at least one RAR/RXR active agent comprises a Retinoic Acid Receptor (RAR) active agent.

Embodiment 14

The method of Embodiment 13 wherein the at least one RAR/RXR active agent is a RAR active agent.

Embodiment 15

The method of Embodiment 13 or 14, wherein the RAR active agent is a RARα antagonist.

Embodiment 16

The method of Embodiment 15, wherein the RAR active agent is a selective RARα antagonist.

Embodiment 17

The method of Embodiment 13 or 14, wherein the RAR active agent is a RARγ agonist.

Embodiment 18

The method of Embodiment 17, wherein the RAR active agent is a selective RARγ agonist.

Embodiment 19

The method of any one of Embodiments 1-13, wherein the at least one RAR/RXR active agent comprises a Retinoid X Receptor (RXR) active agent.

Embodiment 20

The method of Embodiment 19, wherein the at least one RAR/RXR agent is a Retinoid X Receptor (RXR) active agent.

Embodiment 21

The method of embodiment 20, wherein the RXR active agent is a RXR antagonist.

Embodiment 22

The method of any one of Embodiments 1-21, wherein the at least one RAR/RXR active agent comprises at least two RAR active agents.

Embodiment 23

The method of Embodiment 22, wherein a first RAR active agent is a RARα antagonist, and a second RAR active agent is a RARγ selective agonist.

Embodiment 24

The method of Embodiment 22, wherein a first RAR active agent is a RARα selective antagonist, and a second RAR active agent is a RARγ agonist.

Embodiment 25

The method of Embodiment 22, wherein a first RAR active agent is a RARα selective antagonist, and a second RAR active agent is a RARγ selective agonist.

Embodiment 26

The method of any one of Embodiments 9, 15-16, or 23-25, wherein the RARα antagonist is a compound of general formula (I)

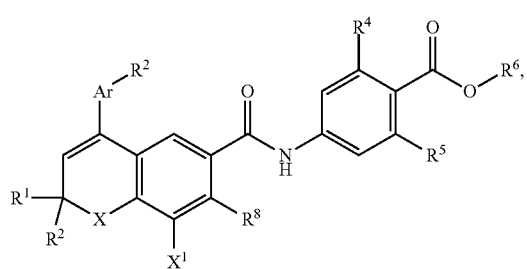

(I)

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH.

Embodiment 27

The method of Embodiment 26, wherein the RARα antagonist is:

AGN 194301

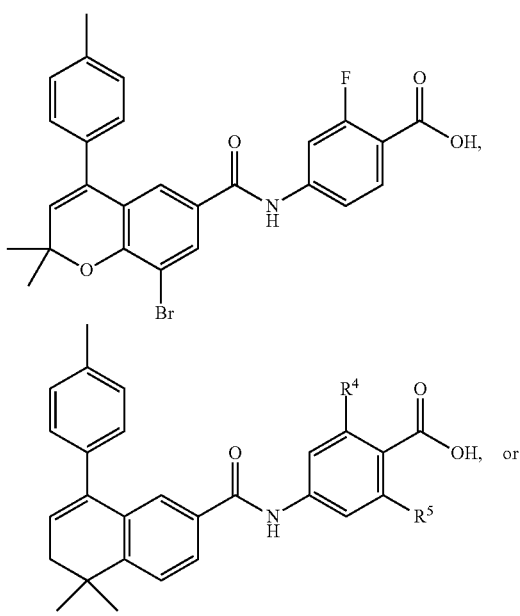

$R^4$ and $R^5$ both H; AGN193491
$R^4$ = F, $R^5$ = H; AGN193618
$R^4$ and $R^5$ both F; AGN194202

AGN 194574

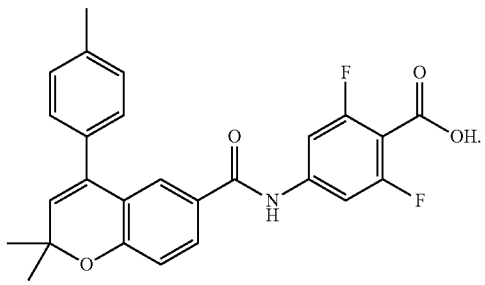

Embodiment 28

The method of any one of Embodiments 9, 15-16, or 23-25, wherein the RARα antagonist is a compound of general formula (II)

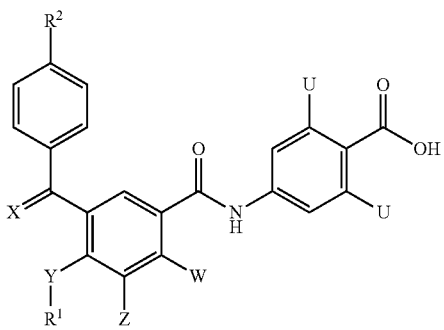

(II)

wherein $R^1$ and $R^2$ are independently $C_{1-6}$ alkyl; X is O, S, or $CH_2$; Y is O, S, $CH_2$, or $NR^3$, wherein $R^3$ is $C_{1-6}$ alkyl; Z is Cl or Br; W is H or OH; and U is independently H or F.

Embodiment 29

The method of Embodiment 28, wherein the RARα antagonist is:

VTP 196696

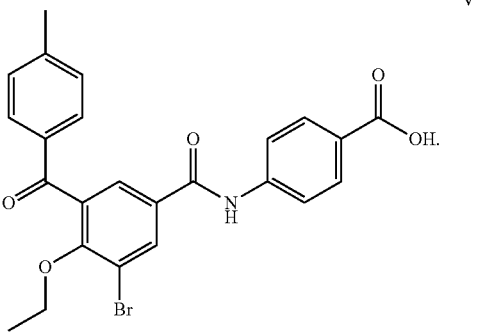

Embodiment 30

The method of any one of Embodiments 9, 15-16, or 23-25, wherein the RARα antagonist is a compound of general formula (III)

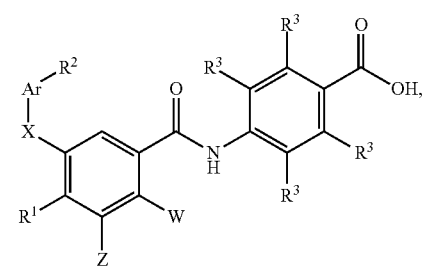

(III)

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br.

Embodiment 31

The method of any one of Embodiments 9, 15-16, or 23-25, wherein the RARα antagonist is BMS185411, BMS614, Ro41-5253, Ro46-5471, or

AGN 194777

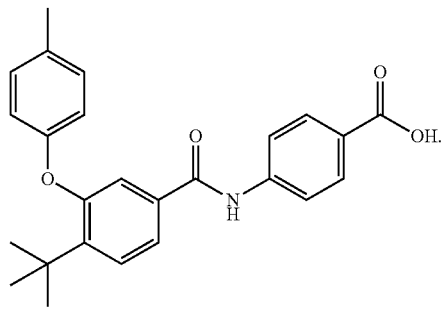

Embodiment 32

The method of any one of Embodiments 9, 15-16, or 23-25, wherein the RARγ agonist is a RARγ agonist of general formula IV (IV)

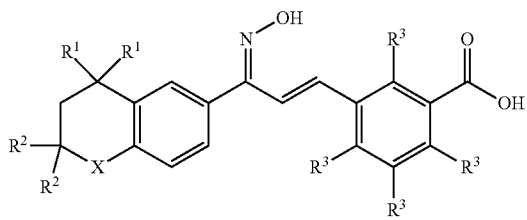

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl.

Embodiment 33

The method of any one of Embodiments 9, 15-16, or 23-25, wherein the RARγ agonist is:

AGN 190183

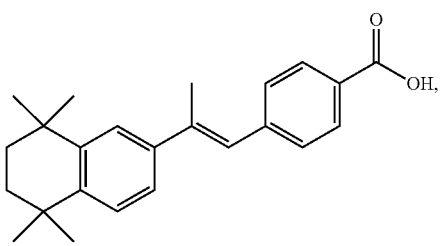

AGN 190205

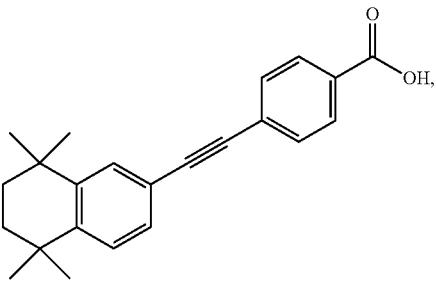

AGN 204647

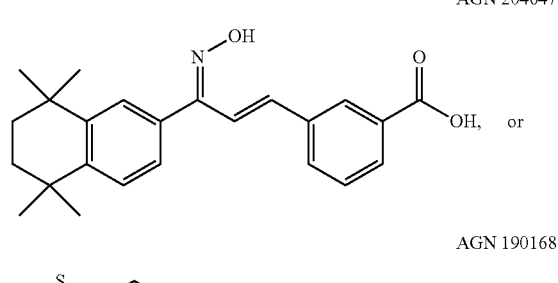

, or

AGN 190168

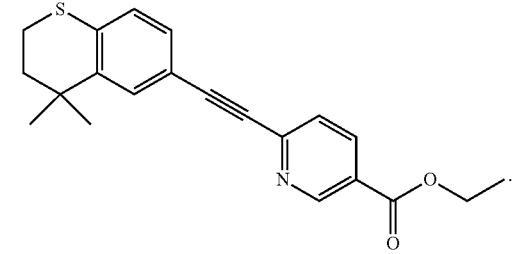

(Tazarotene)

Embodiment 34

The method of any one of Embodiments 9, 15-16, or 23-25, wherein the RARγ agonist is a selective RARγ agonist selected from CD437, CD2325, CD666, and BMS961.

Embodiment 35

The method of any one of Embodiments 9 or 19-20, wherein the RXR antagonist is selected from

HX 531

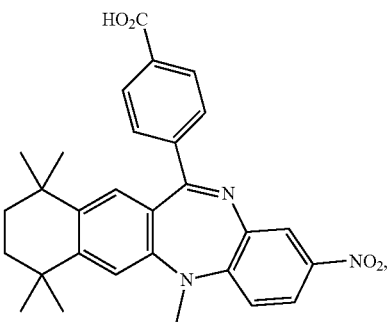

PA 451

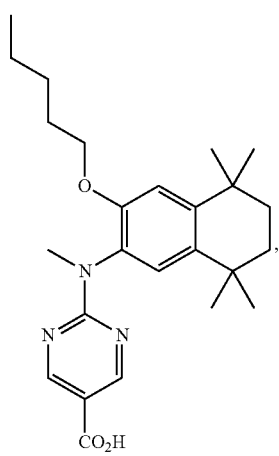

PA 452

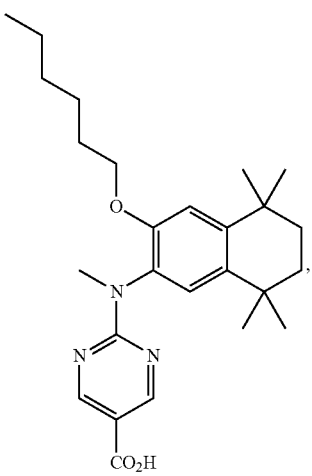

LG 100754

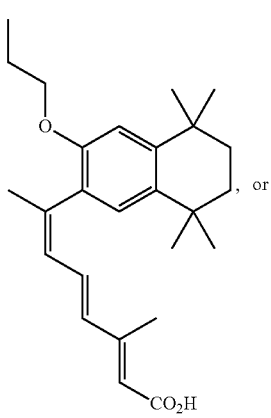

UVI 3003

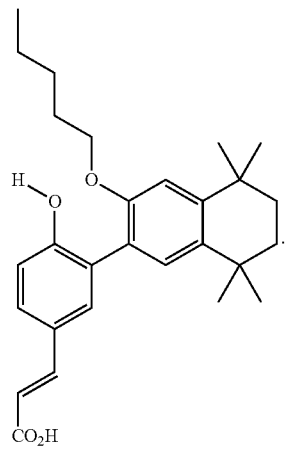

Embodiment 36

The method of any one of Embodiments 9 or 19-20, wherein the RXR antagonist is AGN195393, or LGN100849.

Embodiment 37

The method of any one of Embodiments 1-6 or 8-36, further comprising administering at least one cancer chemotherapy agent.

Embodiment 38

The method of any one of Embodiments 1-6 or 8-37, wherein the subject or patient is pretreated with the at least one RAR/RXR active agent prior to administration of the CAR-MIC.

Embodiment 39

The method of Embodiment 38 wherein the at least one RAR/RXR active agent is administered at least 12 hours before administration of the CAR-MIC.

Embodiment 40

The method of Embodiment 39 wherein the at least one RAR/RXR active agent is administered for at least 1, 2, 3, 4, 5, 6, 7, 8, 9, 10 days before administration of the CAR-MIC.

Embodiment 41

The method of any one of Embodiments 1-6 or 8-40 wherein the subject or patient is treated with the at least one RAR/RXR active agent concurrent with or subsequent to administration of the CAR-MIC.

Embodiment 42

The method of Embodiment 41, wherein treatment (as distinct from pretreatment, if any) commences on the same day as administration or first administration of the CAR-MIC.

Embodiment 43

The method of Embodiment 41, wherein treatment (as distinct from pretreatment, if any) commences 1, 2, 3, 4, 5, 6, or 7 days after administration or first administration of the CAR-MIC.

Embodiment 44

The method of any one of Embodiments 41-43, wherein treatment with the at least one RAR/RXR active agent continues for at least 6 months following administration or 1st administration of the CAR-MIC.

Embodiment 45

The method of any one of Embodiments 41-43, wherein treatment with the at least one RAR/RXR active agent continues until a durable complete response is obtained.

Embodiment 46

The method of any one of Embodiments 41-43, wherein treatment with the at least one RAR/RXR active agent continues as long as there is continued tumor regression.

Embodiment 47

The method of any one of Embodiments 41-43, wherein treatment with the at least one RAR/RXR active agent continues as long as there is stable disease or the cancer does not progress.

Embodiment 48

The method of any one of Embodiments 1-6 or 8-47, wherein the at least one RAR/RXR active agent is administered daily.

Embodiment 49

The method of any one of Embodiments 1-48, wherein the CAR-MIC is a CAR-T cell.

Embodiment 50

The method of any one of Embodiments 1-48, wherein the CAR-MIC is a CAR-NKT cells

Embodiment 51

The method of any one of Embodiments 1-48, wherein the CAR-MIC is a CAR-NK cell.

Embodiment 52

The method of any one of Embodiments 1-48, wherein the CAR-MIC is a CAR-macrophage.

Embodiment 53

One or more RAR/RXR active agents for use in cancer immunotherapy in a patient who is receiving, has received, or is scheduled to receive CAR-MIC, whereby the immunotherapeutic effect of the CAR-MIC is potentiated.

Embodiment 54

CAR-MIC and at least one RAR/RXR active agent for use in cancer immunotherapy.

Embodiment 55

CAR-MIC and at least one RAR/RXR active agent for use in prolonging the disease-free survival of a cancer patient.

Embodiment 56

One or more RAR/RXR active agents for use in reducing the toxicity of CAR-MIC therapy.

Embodiment 57

CAR-MIC and at least one RAR/RXR active agent for use in treating cancer.

Embodiment 58

Use of one or more RAR/RXR active agents in the manufacture of a medicament for potentiating the immunotherapeutic effect of CAR-MIC in the treatment of cancer.

Embodiment 59

Use of CAR-MIC and at least one RAR/RXR active agent in the manufacture of a medicament for cancer immunotherapy.

Embodiment 60

Use of CAR-MIC and at least one RAR/RXR active agent in the manufacture of a medicament for prolonging the disease-free survival of a cancer patient.

Embodiment 61

Use of one or more RAR/RXR active agents in the manufacture of a medicament for reducing the toxicity of CAR-MIC therapy.

Embodiment 62

Use of CAR-MIC and at least one RAR/RXR active agent in the manufacture of a medicament for treating cancer. It should be manifest that each of Embodiments 53-62 can be modified in a manner similar to the modification of Embodiments 1-6 by Embodiments 8-52.

EXAMPLES

The following non-limiting examples are provided for illustrative purposes only in order to facilitate a more complete understanding of representative embodiments now contemplated. These examples should not be construed to limit any of the embodiments described in the present specification.

Example 1

RARα Signaling Induces Foxp3 Expression

Figure 1B:
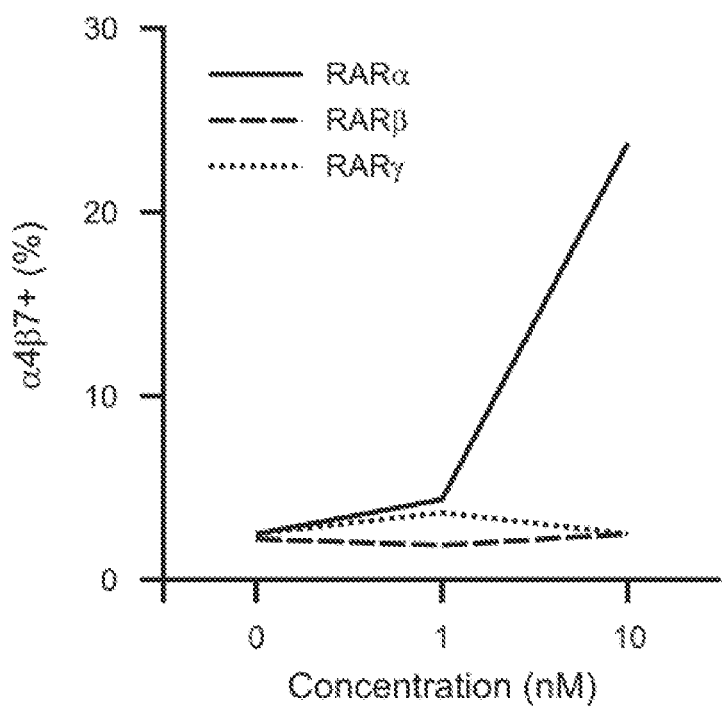

It is important to determine which of the RAR (RARα, RARβ, RARγ) signaling pathways is important in the induction of Foxp3 expression. To determine this, naive CD4$^+$ CD25$^-$ FoxP3$^-$ cells were purified from a Foxp3-GFP mouse using flow cytometry by sorting and isolating based upon a GFP$^-$ phenotype. These cells were activated polyclonally with αCD3 in vitro in the presence of IL-2 and TGF-β. To identify the RAR involved in RA-induced Foxp3 expression, the cultured cells were incubated with RAR selective agonists. The cultured cells were then scored for the frequency of GFP$^+$ (Foxp3$^+$). With respect to the use of selective agonists, only the RARα agonist exerted significant impact on the expression of Foxp3 inducing nearly 100% Foxp3+ T cells, with enhancement on the expression of α4β7 and CCR9 (gut homing receptors) (FIG. 1). The RARγ and RARβ agonists were without effect. These results indicate that RARα selective agonists could be useful in reducing a symptom of inflammation or an autoimmune disorder. Conversely, RARα selective antagonists or inverse agonists could be useful to downregulate the production of immunosuppressive Treg cells thereby promoting an immune response, such as an anti-cancer immune response.

Example 2

Binding of Test Compounds to RAR and RXR Receptors and Activation of Reporter Genes Retinoic acid receptor transactivation activity and binding efficiencies are determined essentially as described in U.S. Pat. Nos. 5,298,429 and 5,071,773, incorporated by reference herein. Transactivation assays employ expression plasmids encoding the full length receptors RARα, RARβ, RARγ, RXRα, RXRβ, and RXRγ. Reporter plasmids containing the herpes virus thymidine kinase promoter and the appropriate retinoic acid receptor response element (RAREs) or retinoid X receptor response element (RXREs) are positioned upstream of an open coding region encoding firefly luciferase.

Binding assays are performed using a classic competition assay format in which cloned receptor RAR and RXR molecules are first loaded with either radiolabeled all-trans-retinoic acid (RAR) or radiolabeled 9-cis retinoic acid (RXR), and then the amount of radioactivity liberated with increasing concentration of test compound is measured.

The assays are used to identify RARα selective antagonists, RARγ selective agonists and RXR selective antagonists as disclosed herein above.

Example 3

Pharmacological Activation of RARγ Signaling Using RARγ Agonists has a Cooperative Effect with Anti-CTLA-4 Antibody in Rejection of B 16 Melanoma Cells The anti-tumor effects of anti-CTLA-4 antibody treatment combined with 10 nM RARγ agonist (AGN204647 (IRX4647)) are examined in C57BL/6 mice engrafted with B16F10 tumor cells. Mice treated with vehicles only do not show a survival advantage (0%) over untreated control mice. The survival rate of the mice treated with anti-CTLA-4 antibody alone is 40% at 50 days while the mice treated with RARγ agonist alone have a 30% survival in the same time. Remarkably, mice treated with both anti-CTLA-4 antibody and RARγ agonist have a 100% survival at 50 days indicating that these two agents cooperate to eliminate the B16 melanoma cells. Surviving mice that undergo combination treatment are resistant to re-challenge with twice the dose of live tumor cells indicating the effective formation of B16-specific memory cells. Importantly, the anti-melanoma effect is obtained with this combination of drugs without signs of acute or delayed toxicity Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of expanding the number of CAR-MIC in vitro comprising culturing the CAR-MIC in a culture medium comprising at least one immunomodulatory retinoid active agent and/or rexinoid active agent (RAR/RXR active agent), wherein the at least one immunomodulatory RAR/RXR active agent is:

a) a RARα antagonist, wherein the RARα antagonist is:
i) a compound of general formula (I)

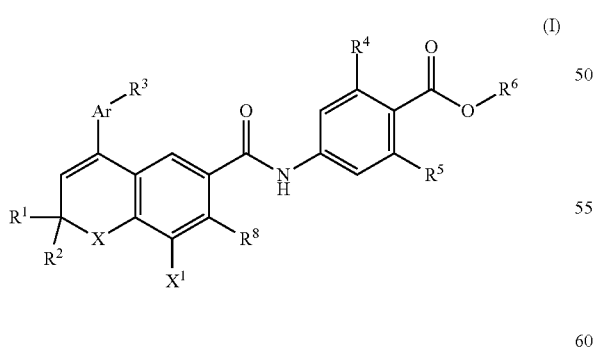

(I)

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH; or ii) a compound of general formula (II)

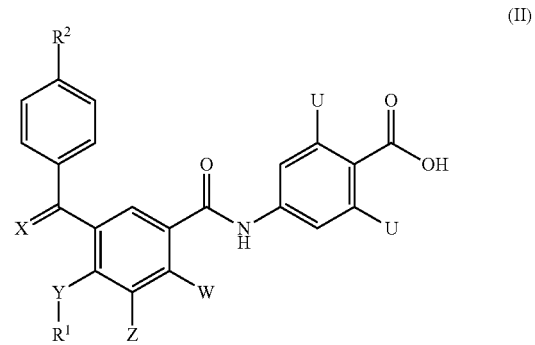

(II)

wherein $R^1$ and $R^2$ are independently $C_{1-6}$ alkyl; X is O, S, or $CH_2$; Y is O, S, $CH_2$, or $NR^3$, wherein $R^3$ is $C_{1-6}$ alkyl; Z is Cl or Br; W is H or OH; and U is independently H or F; or iii) a compound of general formula (III):

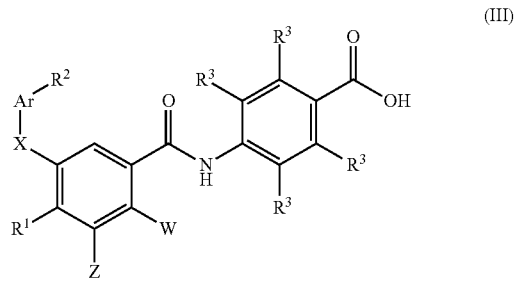

(III)

wherein $R^1$ and $R^2$ are independently H or $C_{1-6}$ alkyl; $R_3$ is H or F; Ar is phenyl, pyridyl, thienyl, furyl, or naphthyl; X is O, S, N, or $CH_2$; W is H or OH; and Z is Cl or Br; or iv) BMS185411, BMS614, Ro41-5253, Ro46-5471, or AGN 194777; or b) a RARγ agonist, wherein the RARγ agonist is:
i) a compound of general formula (IV):

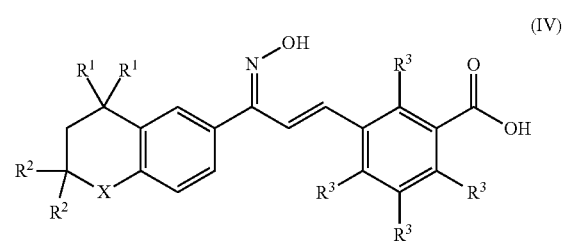

(IV)

wherein $R^1$ and $R^2$ are independently H or $C_{1-6}$ alkyl; $R^3$ is H or F; and X is O, S, $CH_2$, $C(R^4)_2$, or $NR^5$, wherein $R_4$ and $R_5$ are independently H or $C_{1-6}$ alkyl; or ii)
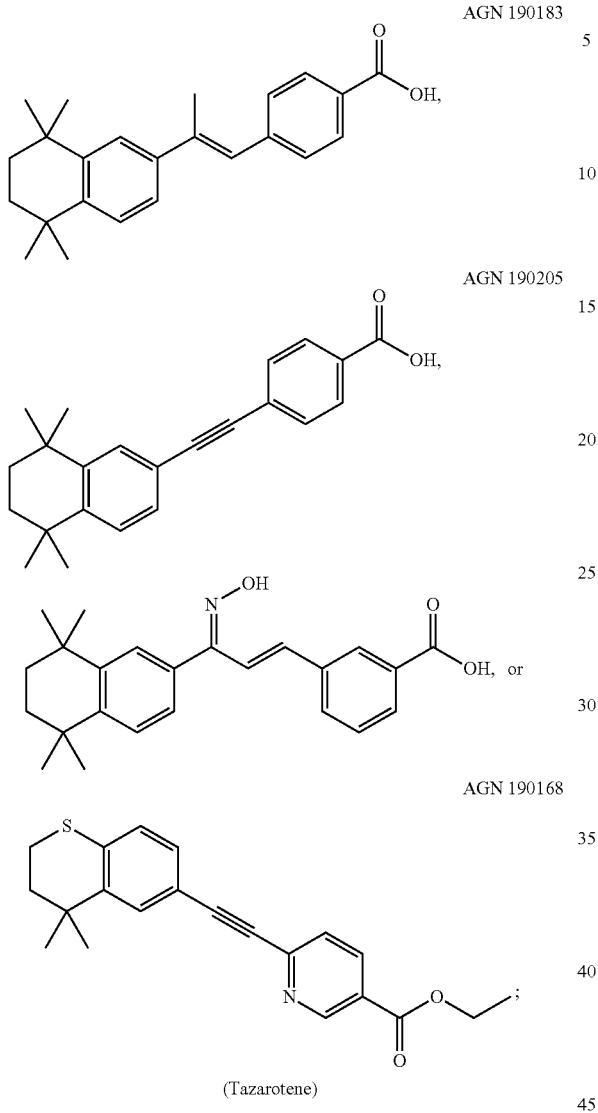
(Tazarotene)
or
iii) CD437, CD2325, CD666, or BMS961; or
c) a RXR antagonist, wherein the RXR antagonist is: AGN195393, LGN100849,
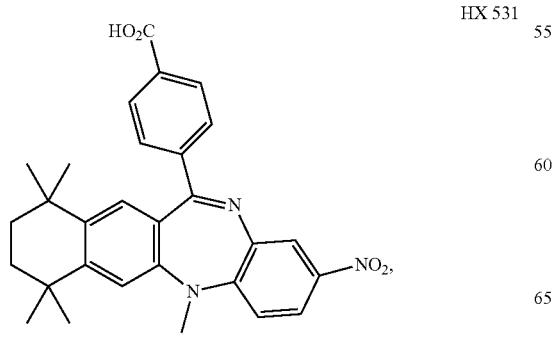
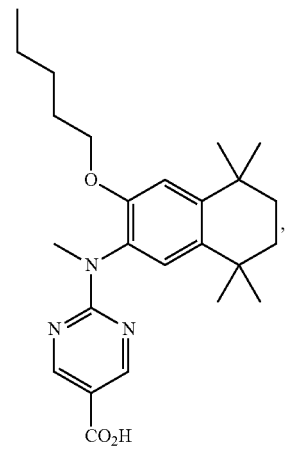
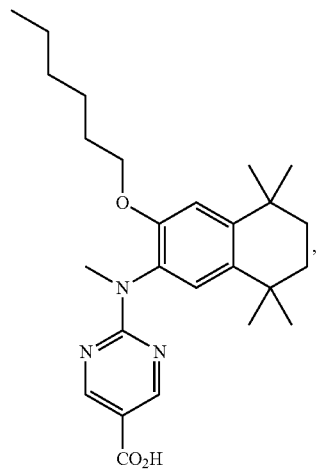
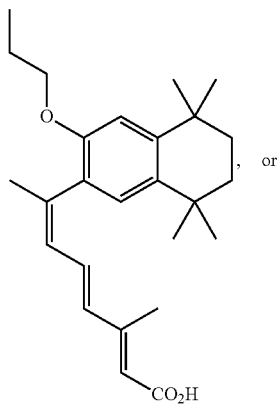

-continued

UVI 3003

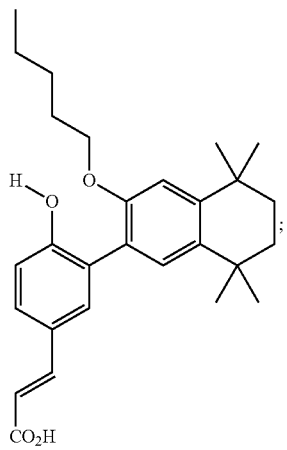

or d) a combination thereof.

2. The method of claim 1, wherein potency of effector cells in the cultured CAR-MIC is increased.

3. The method of claim 1, wherein the at least one RAR/RXR active agent comprises at least two RAR active agents.

4. The method of claim 3, wherein a first RAR active agent is a RARα antagonist, and a second RAR active agent is a RARγ selective agonist.

5. The method of claim 3, wherein a first RAR active agent is a RARα selective antagonist, and a second RAR active agent is a RARγ agonist.

6. The method of claim 1, wherein the RARα antagonist is a compound of general formula (I)

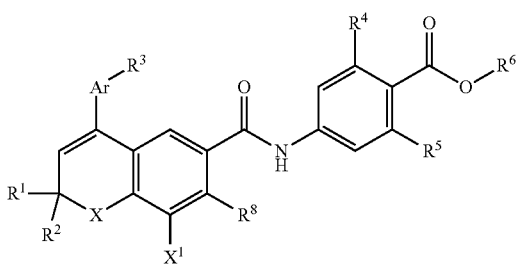

(I)

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R_8$ is H or OH.

7. The method of claim 6, wherein the RARα antagonist is:

AGN 194301

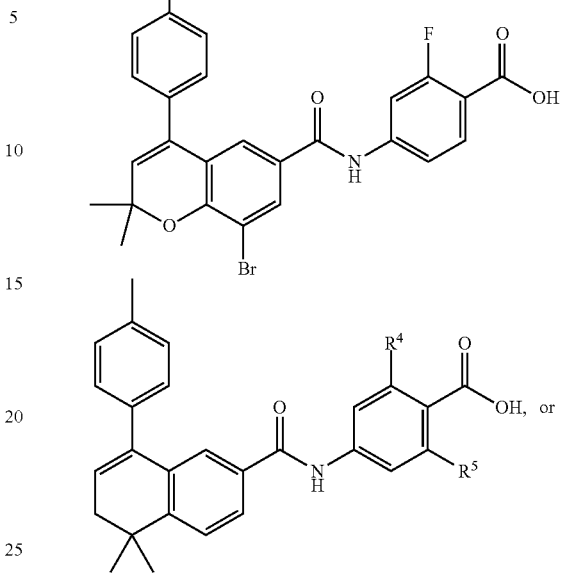

$R^4$ and $R^5$ both H; AGN193491
$R^4$ = F, $R^5$ = H; AGN193618
$R^4$ and $R^5$ both F; AGN194202

AGN 194574

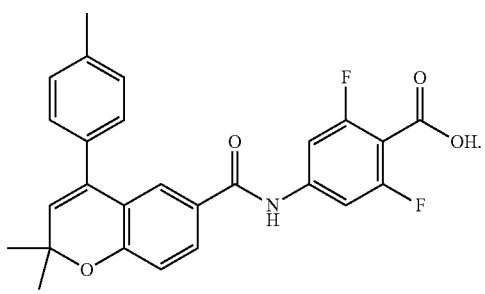

8. The method of claim 1, wherein the RARα antagonist is a compound of general formula (II)

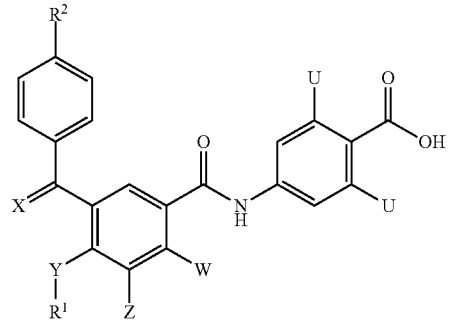

(II)

wherein $R^1$ and $R^2$ are independently $C_{1-6}$ alkyl; X is O, S, or $CH_2$; Y is O, S, $CH_2$, or $NR^3$, wherein $R^3$ is $C_{1-6}$ alkyl; Z is Cl or Br; W is H or OH; and U is independently H or F.

9. The method of claim 8, wherein the RARα antagonist is:

VTP 196696

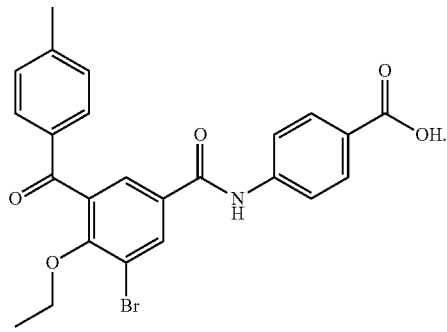

10. The method of claim 1, wherein the RARα antagonist is a compound of general formula (III):

(III)

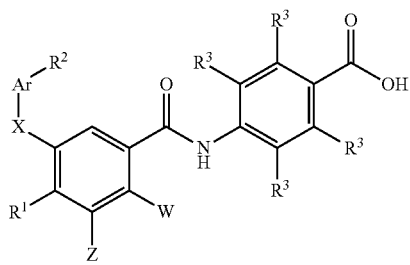

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br.

11. The method of claim 1, wherein the RARα antagonist is BMS185411, BMS614, Ro41-5253, Ro46-5471, or

AGN 194777

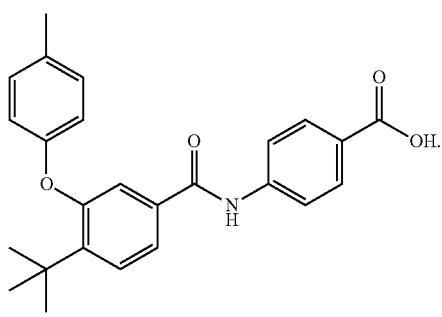

12. The method of claim 1, wherein the RARγ agonist is:

AGN 190183

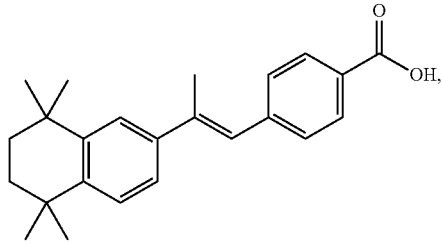

-continued

AGN 190205

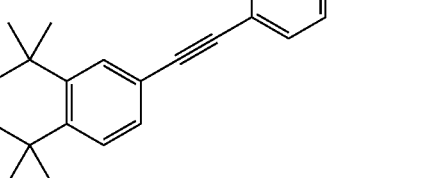

AGN 190168

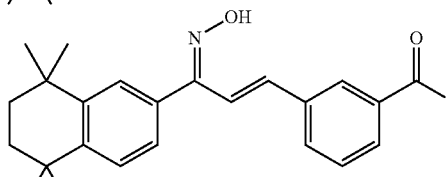

(Tazarotene)

13. The method of claim 1, wherein the RARγ agonist is a RARγ agonist of general formula IV (IV)

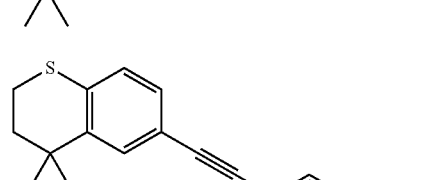

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl.

14. The method of claim 1, wherein the RARγ agonist is a RARγ selective agonist selected from CD437, CD2325, CD666, and BMS961.

15. The method of claim 1, wherein the RXR antagonist is selected from AGN195393, LGN100849,

HX 531

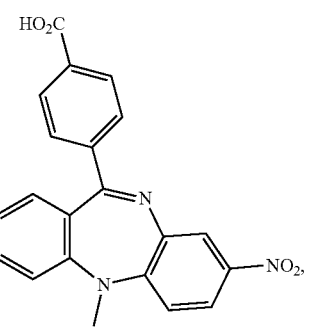

PA 451
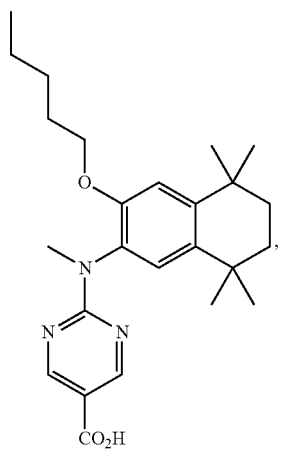
PA 452
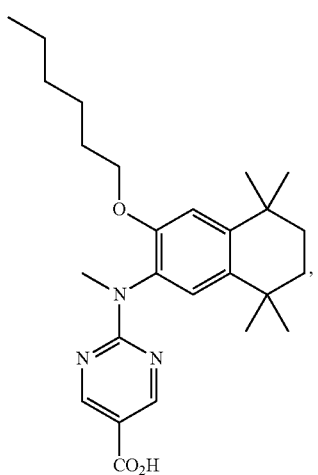
LG 100754
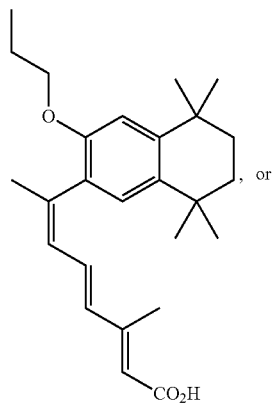
UVI 3003
, or
H O
CO₂H
16. The method of claim 1, wherein the CAR-MIC is a CAR-T cell.
17. The method of claim 1, wherein the immunomodulatory RAR/RXR active agent promotes the development Th17 cells or suppresses the development of Treg cells.
* * * * *